US009618504B2

(12) United States Patent
Hirata et al.

(10) Patent No.: US 9,618,504 B2
(45) Date of Patent: Apr. 11, 2017

(54) SAMPLE ANALYZER

(71) Applicant: SYSMEX CORPORATION, Kobe-shi, Hyogo (JP)

(72) Inventors: Tsukasa Hirata, Kakogawa (JP); Shoichiro Asada, Akashi (JP); Naoya Maeda, Kanzaki-gun (JP); Kosuke Yamaguchi, Kobe (JP)

(73) Assignee: SYSMEX CORPORATION, Kobe-shi (JP)

( * ) Notice: Subject to any disclaimer, the term of this patent is extended or adjusted under 35 U.S.C. 154(b) by 0 days.

(21) Appl. No.: 14/226,249

(22) Filed: Mar. 26, 2014

(65) Prior Publication Data
US 2014/0295453 A1 Oct. 2, 2014

(30) Foreign Application Priority Data

Mar. 29, 2013 (JP) .................. 2013-071429

(51) Int. Cl.
G01N 33/00 (2006.01)
G01N 33/53 (2006.01)
G01N 35/00 (2006.01)

(52) U.S. Cl.
CPC ... *G01N 33/5302* (2013.01); *G01N 35/00584* (2013.01); *G01N 35/00693* (2013.01); *G01N 2035/00673* (2013.01); *G01N 2035/00891* (2013.01)

(58) Field of Classification Search
CPC ............. G01N 33/5302; G01N 35/584; G01N 35/693; G01N 2035/673
See application file for complete search history.

(56) References Cited

U.S. PATENT DOCUMENTS

| 5,428,993 | A | 7/1995 | Kobashi |
| 2007/0212261 | A1 | 9/2007 | Tanaka et al. |
| 2008/0056939 | A1 | 3/2008 | Awata et al. |
| 2008/0063570 | A1 | 3/2008 | Fujino et al. |
| 2009/0163367 | A1 | 6/2009 | Yoo |
| 2010/0114501 | A1 | 5/2010 | Kondou et al. |
| 2010/0210019 | A1 | 8/2010 | Kurono et al. |
| 2011/0223077 | A1 | 9/2011 | Tanaka et al. |

(Continued)

FOREIGN PATENT DOCUMENTS

| EP | 2 410 340 A1 | 1/2012 |
| JP | 01-105165 A | 4/1989 |

(Continued)

*Primary Examiner* — Sam P Siefke
(74) *Attorney, Agent, or Firm* — Mots Law, PLLC

(57) ABSTRACT

To provide a sample analyzer capable of accurately obtaining the number of analyzable samples. When analyzing a sample collected from a subject, a CPU of the sample analyzer calculates the number of analyzable samples based on a remaining number of tests of a reagent set in a reagent holding section and the number of tests of the reagent to be consumed in measurement of a control, and causes a output section to display the number of analyzable samples. When creating a calibration curve, the CPU calculates the number of analyzable samples based on a remaining number of tests of the reagent set in the reagent holding section, the number of tests of the reagent to be consumed in measurement of the control, and the number of tests of the reagent to be consumed in measurement of a calibrator, and causes the output section to display the number of analyzable samples.

14 Claims, 16 Drawing Sheets

(56) References Cited

U.S. PATENT DOCUMENTS

2012/0109529 A1  5/2012  Ariyoshi

FOREIGN PATENT DOCUMENTS

| JP | H05-084864 U | 11/1993 |
|----|--------------|---------|
| JP | 10-010134 A  | 1/1998  |
| JP | 2000-321283 A | 11/2000 |
| JP | 2008-051570 A | 3/2008  |
| JP | 2008-052570 A | 3/2008  |
| JP | 2008-70115 A | 3/2008  |
| JP | 2008-145124 A | 6/2008  |
| JP | 2008-197091 A | 8/2008  |
| JP | 2008-209138 A | 9/2008  |
| JP | 2008-224243 A | 9/2008  |
| JP | 2009-036513 A | 2/2009  |
| JP | 2009-168730 A | 7/2009  |

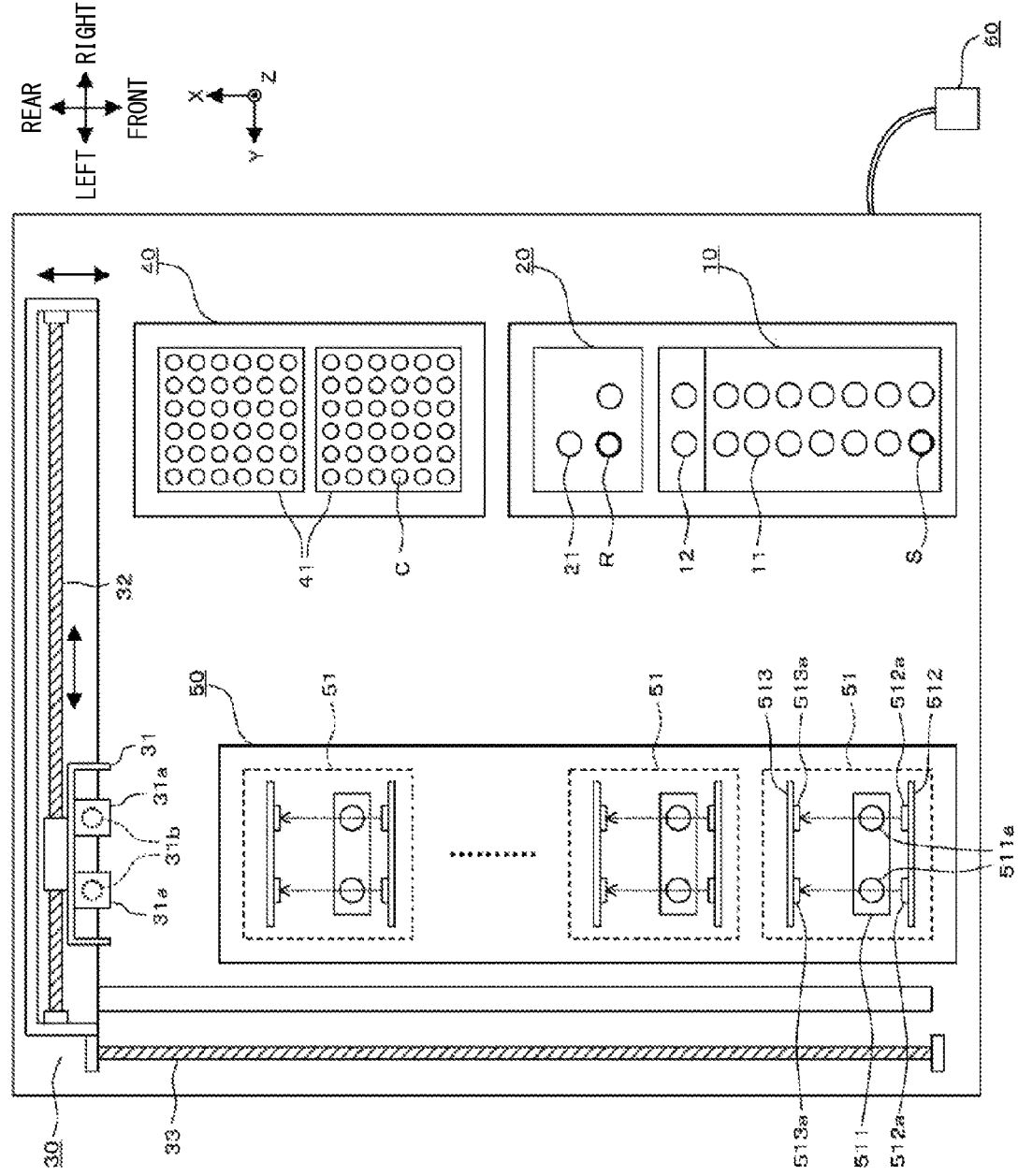
F I G. 2

FIG. 6

```
                            CONFIRMATION
Reagent information is registered as indicated below.  Since the lot number
is different from the registered lot number, other reagent information and
quality control information will be cleared.
```

D1

| | | | | |
|---|---|---|---|---|
| REAGENT CODE : ZS10021001 LOT NUMBER : ZS1002 EXPIRATION DATE : 2013/10/31 OFFSET TIME : 96sec | | DATE OF OPENING 2013/03/15 | | |
| MELTING | 1 − + | TIMES | | |
| CK19 PR REMAINING AMOUNT | 6(2) sample | 30 − + | test | |
| ENZYME | 6(2) sample | 30 − + | test | |
| | | | OK | CANCEL |

FIG. 9A

| ORDER REGISTRATION | | | | |
|---|---|---|---|---|
| GROUP | BATCH NUMBER | REAGENT INFORMATION | | |
| Calibrator ▽ | 1 | LOT/VIAL ZS1002 / 100-1 <br> EXPIRATION DATE 2013/04/15  MELTING 3 TIMES <br> EXPIRATION DATE AFTER OPENING  2013/04/15 | | |

CONTROL INFORMATION

| POSITION | SAMPLE ID |
|---|---|
| PC | QC-[CK19-PC] |
| NC | QC-[NC] |

| PRIMER (CK19) | 20 SAMPLE | ENZYME | 49 SAMPLE |
|---|---|---|---|

ORDER INFORMATION

| POSITION | SAMPLE ID | COMMENT |
|---|---|---|
| C3 | STD-[C3] | |
| C2 | STD-[C2] | |
| C1 | STD-[C1] | |

▷ START

F I G. 9 B

| POSITION | SAMPLE ID |
|---|---|
| PC | QC-[CK19-PC] |
| PC | QC-[Bact-PC] |
| NC | QC-[NC] |

GROUP: Calibrator ▽

BATCH NUMBER: 1

REAGENT INFORMATION

LOT/VIAL ZS1002 / 100-1
EXPIRATION DATE 2013/04/15  MELTING 3 TIMES
EXPIRATION DATE AFTER OPENING 2013/04/15

PRIMER (CK19) 18 SAMPLE
ENZYME 27 SAMPLE

ORDER REGISTRATION

CONTROL INFORMATION

ORDER INFORMATION

| POSITION | SAMPLE ID | COMMENT |
|---|---|---|
| CC | STD-[CC] | |
| C3 | STD-[C3] | |
| C2 | STD-[C2] | |
| C1 | STD-[C1] | |

▷ START

FIG. 13A

| | | | ORDER REGISTRATION | |
|---|---|---|---|---|
| GROUP | | BATCH NUMBER | REAGENT INFORMATION | |
| Sample ▽ | | 1 | LOT/VIAL ZS1002 / 100-1 | |
| | | | EXPIRATION DATE 2013/04/15 | MELTING 3 TIMES |
| CONTROL INFORMATION | | | EXPIRATION DATE AFTER OPENING 2013/04/15 | |

| POSITION | SAMPLE ID |
|---|---|
| PC | QC-[CK19-PC] |
| NC | QC-[NC] |

| PRIMER (CK19) | 21 SAMPLE | ENZYME | 50 SAMPLE |
|---|---|---|---|

ORDER INFORMATION

| POSITION | SAMPLE ID | COMMENT |
|---|---|---|
| 7 | | |
| 6 | | |
| 5 | | |
| 4 | | |
| 3 | | |
| 2 | | |
| 1 | | |

> START

F I G. 1 3 B

| GROUP | BATCH NUMBER | REAGENT INFORMATION |
|---|---|---|
| Sample ▽ | 1 | LOT/VIAL   ZS1002 / 100-1<br>EXPIRATION DATE  2013/04/15   MELTING 3 TIMES<br>EXPIRATION DATE AFTER OPENING  2013/04/15 |

CONTROL INFORMATION

| POSITION | SAMPLE ID |
|---|---|
| PC | QC-[CK19-PC] |
| PC | QC-[Bact-PC] |
| NC | QC-[NC] |

PRIMER (CK19)  20 SAMPLE    ENZYME  28 SAMPLE

ORDER INFORMATION

| POSITION | SAMPLE ID | COMMENT |
|---|---|---|
| 4 | | |
| 3 | | |
| 2 | | |
| 1 | | |

▷ START (labels: D52, A522, C56, A521, S521, S522, A523, C55, ORDER REGISTRATION)

FIG. 15

| V | MEASUREMENT DATE | MEASUREMENT TIME | SAMPLE ID | Bat. | Err | CK19 Q. | S/P |
|---|---|---|---|---|---|---|---|
|   | 2013/01/18 | 17:14:26 | Sample02 | 3 |   | (Neg.) | 1 |
|   | 2013/01/18 | 17:16:35 | Sample03 | 3 |   | (Pos.) | 2 |
| V | 2013/01/18 | 17:18:45 | Sample04 | 3 |   | (Pos.) | 3 |
| V | 2013/01/18 | 17:20:57 | Sample05 | 3 |   | (Pos.) | 4 |
|   | 2013/01/18 | 17:23:10 | Sample06 | 3 |   | (Pos.) | 5 |
|   | 2013/01/18 | 17:25:22 | Sample07 | 3 |   | (Pos.) | 6 |
|   | 2013/01/18 | 17:27:35 | QC-[CK19-PC] | 3 |   | (Pos.) | 7 |
|   | 2013/01/18 | 17:27:35 | QC-[NC] | 3 |   | (Neg.) | 7 |
|   | 2013/01/31 | 10:10:59 | STD-[C1] | 1 |   | (Pos.) | 0 |
|   | 2013/01/18 | 10:13:15 | STD-[C2] | 1 |   | (Pos.) | 1 |
|   | 2013/01/18 | 10:15:26 | STD-[C3] | 1 |   | (Pos.) | 2 |

VALIDATE

D6

A6

START

SAMPLE ANALYZER

FIELD OF THE INVENTION

The present invention relates to a sample analyzer, a sample analysis method, and at least one non-transitory storage medium storing a computer program for analyzing samples collected from subjects.

BACKGROUND

To date, there has been known a sample analyzer which mixes a sample collected from a subject and a reagent together to prepare a measurement specimen and measures this measurement specimen, to analyze the sample. In such a sample analyzer, since a reagent contained in a reagent container is used in the measurement, it is important for a user to know how many samples can be analyzed with the reagent remaining in the reagent container, in order to perform efficient sample analysis.

US Patent Application publication No. 2010/114501 discloses a sample analyzer which displays how many more times sample measurement can be performed. The sample analyzer disclosed in US Patent Application publication No. 2010/114501 performs sample measurement for one measurement item by using a plurality of types of reagents. This sample analyzer obtains a remaining number of tests being a measurable number of times for each of the plurality of reagents to be used in measurement of the measurement item mentioned above, and displays the smallest remaining number of tests among remaining numbers of tests of the respective types of reagents, as a measurable number of times of the measurement item.

In a sample analyzer, a reagent is consumed not only each time a sample collected from a subject is analyzed, but also each time measurement is performed on a substance, being different from a sample collected from a subject, such as a calibrator, a quality control sample, water, or the like, in order to perform calibration curve creation, quality control, blank check, or the like. However, in the sample analyzer disclosed in Patent Literature 1, when a reagent is consumed in order to perform calibration curve creation, quality control, blank check, or the like as described above, the displayed measurable number of times does not match an actual number of measurable samples, which causes a problem that the number of measurable samples cannot be accurately obtained.

SUMMARY OF THE INVENTION

The scope of the present invention is defined solely by the appended claims, and is not affected to any degree by the statements within this summary.

A first aspect of the present invention is a sample analyzer comprising:
 a reagent holding section configured to hold a reagent;
 a measurement section configured to measure a first measurement specimen which is prepared from a subject sample collected from a subject and the reagent held by the reagent holding section, and to measure a second measurement specimen which is prepared from a standard specimen different from the subject sample and the reagent held by the reagent holding section;
 an output section, and
 a controller programmed to perform operations, comprising:
  causing the output section to output an analysis result of the subject sample obtained by the measurement section measuring the first measurement specimen; and
  causing the output section to output the number of analyzable subject samples based on an amount of the reagent required to prepare the first measurement specimen and an amount of the reagent to be consumed in measurement of the second measurement specimen.

A second aspect of the present invention is a sample analysis method comprising:
 measuring a first measurement specimen which is prepared from a subject sample collected from a subject and a reagent, and measuring a second measurement specimen which is prepared from a standard specimen different from the subject sample and the reagent;
 outputting an analysis result of the subject sample obtained by measuring the first measurement specimen; and
 outputting the number of analyzable subject samples based on an amount of the reagent required to prepare the first measurement specimen and an amount of the reagent to be consumed in measurement of the second measurement specimen.

A third aspect of the present invention is at least one non-transitory storage medium which stores programs executable collectively by at least one processor of a sample analyzer to perform processes, the sample analyzer comprising a reagent holding section configured to hold a reagent, a measurement section, an output section and the processor, the processes comprising:
 causing the measurement section to measure a first measurement specimen which is prepared from a subject sample collected from a subject and a reagent held by the reagent holding section, and to measure a second measurement specimen which is prepared from a standard specimen different from the subject sample and the reagent held by the reagent holding section;
 causing the output section to output an analysis result of the subject sample obtained by measurement of the first measurement specimen; and
 causing the output section to output the number of analyzable subject samples based on an amount of the reagent required to prepare the first measurement specimen and an amount of the reagent to be consumed in measurement of the second measurement specimen.

BRIEF DESCRIPTION OF THE DRAWINGS

FIG. 2 is a schematic plan view showing a structure of the inside of the sample analyzer according to the embodiment;

FIG. 6 shows a reagent registration dialogue;

FIG. 9A shows a calibration curve creation order registration screen in a 2-item measurement mode;

FIG. 9B is a calibration curve creation order registration screen in a 3-item measurement mode;

FIG. 13A shows a sample analysis order registration screen in the 2-item measurement mode;

FIG. 13B shows a sample analysis order registration screen in the 3-item measurement mode;

FIG. 15 shows an analysis result screen.

DETAILED DESCRIPTION OF THE PREFERRED EMBODIMENTS

The preferred embodiments of the present invention will be described hereinafter with reference to the drawings.

Hereinafter, a sample analyzer 1 according to the present embodiment will be described with reference to the drawings.

<Configuration of Sample Analyzer 1>

Figure 1:
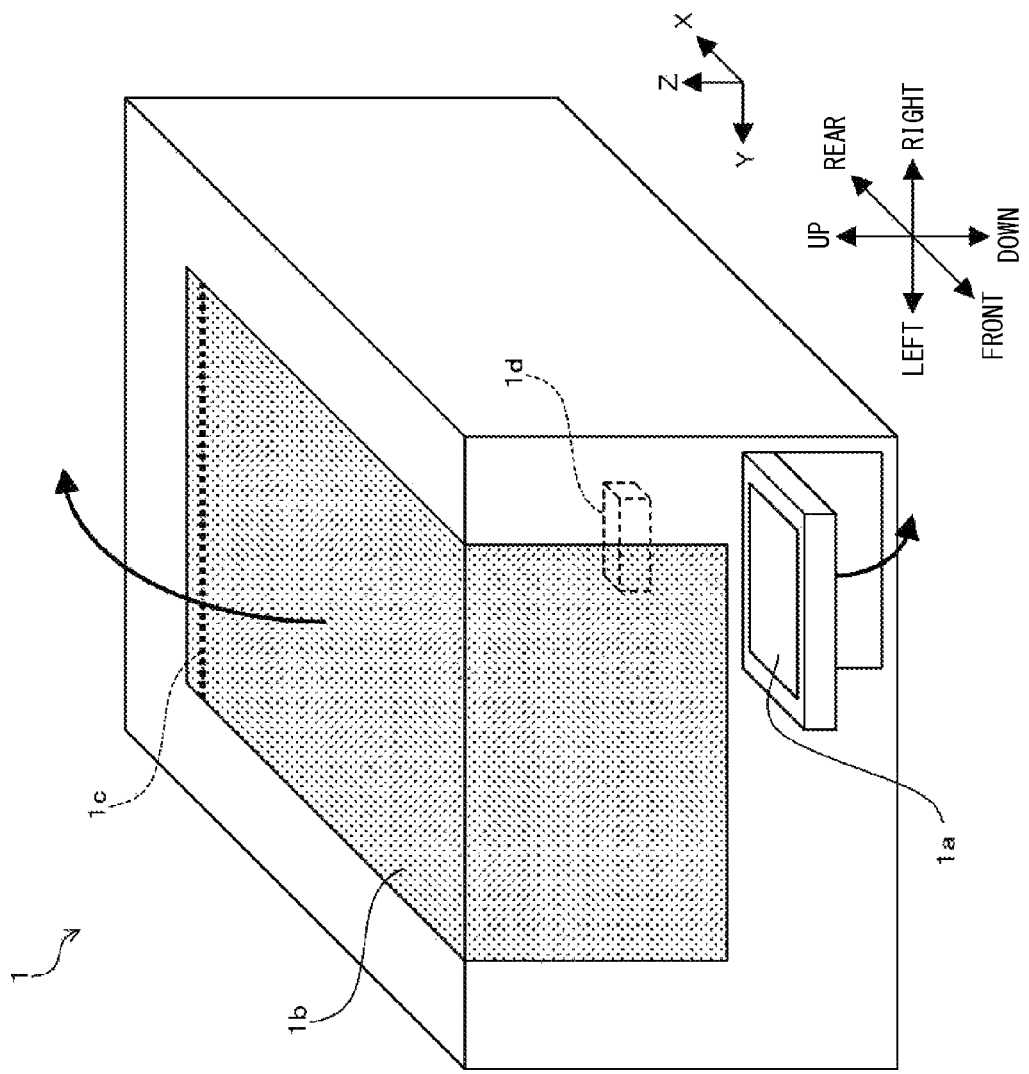
FIG. 1 is a schematic perspective view showing an external structure of a sample analyzer according to an embodiment.

FIG. 1 is a schematic perspective view showing an external structure of the sample analyzer 1.

The sample analyzer 1 is a gene amplification measuring apparatus which performs detection by: using a cancer-derived gene (mRNA) present in excised tissue as a template to amplify nucleic acid based on the LAMP (Loop-mediated Isothermal Amplification, Eiken Chemical Co., Ltd.) method; and measuring turbidity of the solution occurring associated with the amplification. The details of the LAMP method are disclosed in U.S. Pat. No. 6,410,278.

The sample analyzer 1 includes a output section 1*a* composed of a touch panel, and a cover 1*b* extending from the front face to the top face of the sample analyzer 1. The cover 1*b* is configured to be able to rotate about a shaft 1*c*, and is switched by a lock mechanism 1*d* between a locked state and an unlocked state. A user opens an upper portion of the sample analyzer 1 by rotating the cover 1*b* upwardly from the state shown in FIG. 1 while the cover 1*b* is in the unlocked state, thereby being able to access the inside of the sample analyzer 1. Near the lock mechanism 1*d*, a sensor (not shown) for detecting whether the cover 1*b* is closed is provided.

The sample analyzer 1 is provided with a bar code reader 60. The bar code reader 60 is used for registration of reagent information described later.

FIG. 2 is a schematic plan view showing a structure of the inside of the sample analyzer 1.

The sample analyzer 1 includes, inside thereof, a sample container setting section 10, a reagent holding section 20, a dispensing part 30, a tip setting section 40, and a measurement section 50.

On the top face of the sample container setting section 10, 14 holding holes 11 and two holding holes 12 each having an open top are formed. The holding holes 11 are arranged in two rows in the left-right direction and seven in the front-rear direction. The two holding holes 12 are arranged side by side in the left-right direction.

In a holding hole 11, a sample container S containing a solubilized extract (hereinafter, may be referred to as "sample") prepared by subjecting in advance an excised tissue to homogenization, centrifugation, and filtration as pretreatment, or a sample container S containing a diluted sample is set. As pretreatment for preparing, from an excised tissue, a solubilized extract as a specimen for nucleic acid amplification reaction, a method disclosed in US Patent Application publication No. 2006/0121515 can be used. At this time, a sample container S containing a sample prepared from one excised tissue and a sample container S containing a diluted sample obtained by diluting the sample are set in holding holes 11 adjacent to each other in the left-right direction. In the two holding holes 12, a sample container S containing a positive control (positive quality control sample) used in positive quality control for confirming that nucleic acid that should be amplified is amplified normally, and a sample container S containing a negative control (negative quality control sample) used in negative quality control for confirming that nucleic acid that should not be amplified is not amplified normally are set.

When a calibration curve is to be created, before a sample is measured (for example, immediately after activation of the apparatus), sample containers S are set in predetermined holding holes 11, the sample containers S containing calibrators (calibration curve creation sample) which each include a target gene at a predetermined concentration and based on which a calibration curve is created. Also in this case, measurement is performed in a similar manner to sample measurement described later, whereby a calibration curve is created.

In the top face of the reagent holding section 20, three holding holes 21 each having an open top are formed. In a front side portion of the reagent holding section 20, two holding holes 21 arranged in the left-right direction are provided, and in a rear side portion of the reagent holding section 20, one holding hole 21 is provided. In the left holding hole on the front side, a reagent container R which contains a primer reagent containing primers for cytokeratin 19 (CK19) is set. In the right holding hole 21 on the front side, a reagent container R which contains a primer reagent containing primers for beta actin (β-actin) is set. In the rear holding hole 21, a reagent container R is set which contains an enzyme reagent containing an enzyme, for promoting nucleic acid amplification reaction, that is commonly used for nucleic acid amplification reaction of CK19 and nucleic acid amplification reaction of beta actin.

For each holding hole 11 in the sample container setting section 10, a sensor not shown is provided, and by a detection signal from this sensor, whether a sample container S is set in a corresponding holding hole 11 is detected. Similarly to the holding hole 11, for each holding hole 12 in the sample container setting section 10, and each holding hole 21 in the reagent holding section 20, a sensor not shown is provided. By detection signals of the sensors, whether a sample container S is set in a corresponding holding hole 12 and whether a reagent container R is set in a corresponding holding hole 21 are detected.

With reference back to FIG. 2, the dispensing part 30 includes an arm part 31, a shaft 32 extending in the left-right direction, and a shaft 33 extending in the front-rear direction, and a mechanism for moving the arm part 31. The arm part 31, supported by the shaft 32, is movable in the left-right direction, and the mechanism including the arm part 31 and the shaft 32, supported by the shaft 33, is movable in the front-rear direction. The arm part 31 includes two syringe parts 31*a* each independently movable in the up-down direction (Z axis direction) relative to the arm part 31. Each syringe part 31*a* includes, at its lower end (end on the Z axis negative direction side), a nozzle part 31*b* to which a pipette tip C is attached. The syringe part 31a also includes a pump part (not shown) for performing aspiration and discharge.

In the tip setting section 40, two racks 41 each holding 36 pipette tips C are set. The arm part 31 of the dispensing part 30 is moved in the front-rear and left-right directions inside the sample analyzer 1, and each syringe part 31a is moved in the up-down direction, whereby a pipette tip C is attached to the lower end of the nozzle part 31b. Each time operation of aspiration/discharge ends, the pipette tip C attached to the nozzle part 31b is discarded into a discard part (not shown).

The measurement section 50 is composed of eight reaction detection blocks 51 arranged in the front-rear direction. For convenience, in FIG. 2, only some of the eight reaction detection blocks 51 are shown. Each of the eight reaction detection blocks 51 includes a reaction container setting part 511, and base plates 512 and 513 each having a face parallel to the YZ plane. On the top face of the reaction container setting part 511, two holding holes 511a each having an open top are formed. In the two holding holes 511a, a reaction container M for mixing a reagent and a sample together is set.

On the rear side face of the base plate 512, two light-emitters 512a are provided. On the front side face of the base plate 513, two light-receivers 513a are provided. Each light-emitter 512a emits light having a diameter of about 1 mm. Light emitted from the left light-emitter 512a of the base plate 512 is received by the left light-receiver 513a of the base plate 513. Light emitted from the right light-emitter 512a of the base plate 512 is received by the right light-receiver 513a of the base plate 513.

Figure 3:
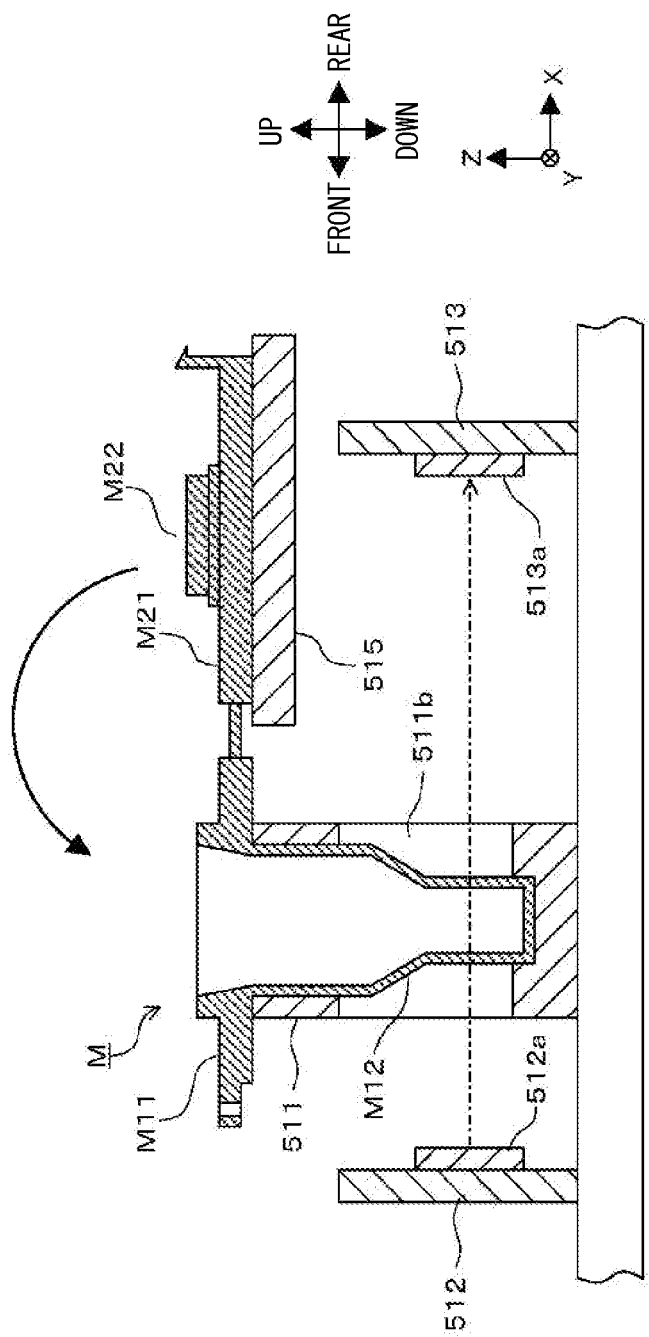
FIG. 3 is a side cross-sectional view showing a structure of a reaction detection block.

FIG. 3 is a side cross-sectional view showing a structure of the reaction detection block 51.

A reaction container M is provided with two receptacles M12, and each of these receptacles M12 can hold a sample and a reagent. Moreover, the reaction container M includes a container body part M11 in which the receptacles M12 are provided, and a cap part M21. The cap part M21 is rotatably connected to the container body part M11.

Each reaction detection block 51 is provided with a cap holding member 515. The cap holding member 515 is capable of holding the cap part M21 of the reaction container M. The cap holding member 515 is also rotatable by a drive mechanism not shown. The cap part M21 is provided with caps M22 respectively corresponding to the two receptacles M12. When the cap part M21 held by the cap holding member 515 rotates relative to the container body part M11, the caps M22 are fit into the respective receptacles M12, whereby the cap of the reaction container M can be closed.

In a lower part of the reaction container setting part 511, holes 511b each passing through the reaction container setting part 511 in the front-rear direction (X axis direction) are formed. Each hole 511b communicates with a corresponding holding hole 511a of the reaction container setting part 511. Light emitted from a corresponding light-emitter 512a transmits through a corresponding receptacle M12 when passing through the hole 511b, to be received by a corresponding light-receiver 513a.

Figure 4:
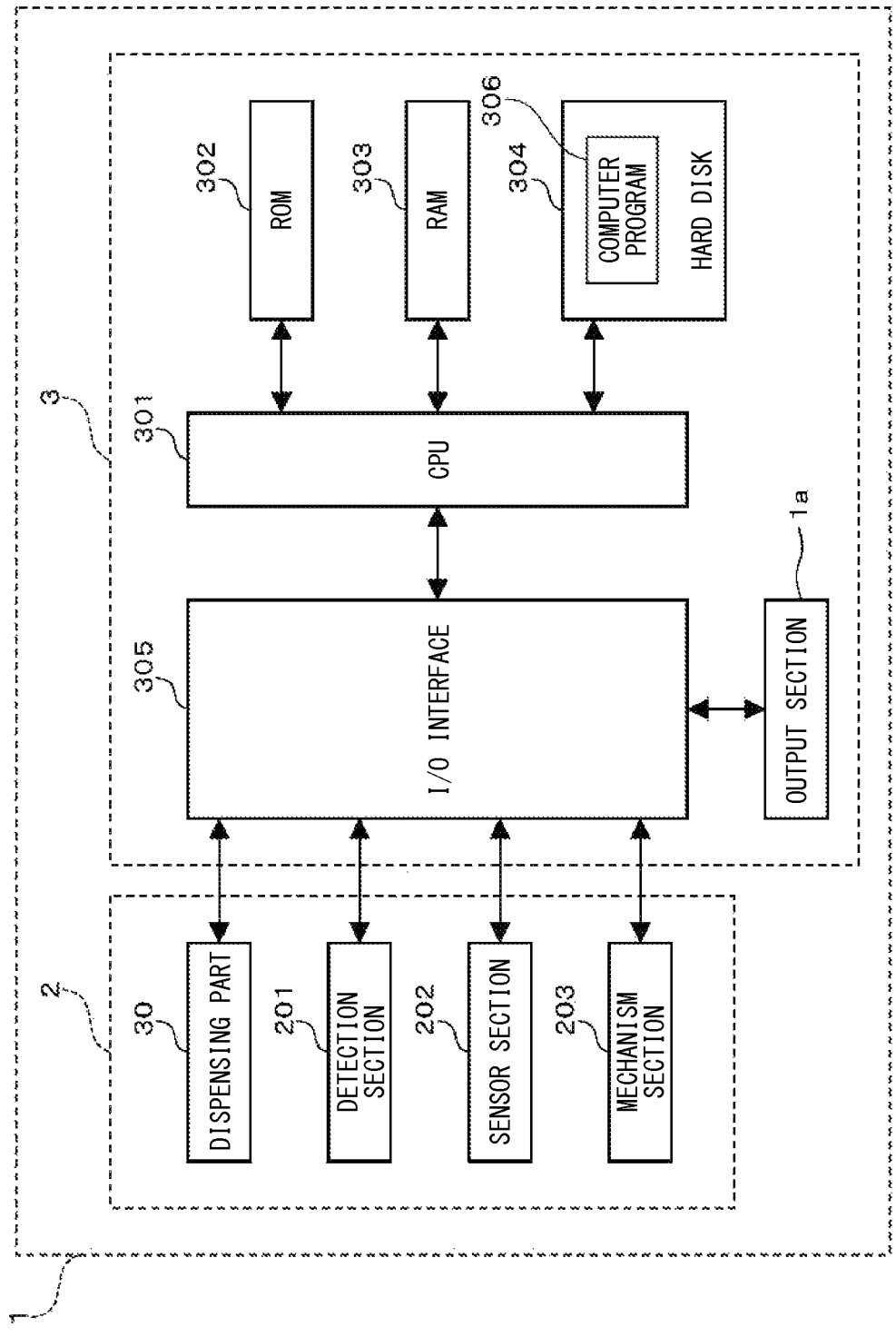
FIG. 4 is a block diagram showing a configuration of the sample analyzer according to the embodiment.

FIG. 4 is a block diagram showing a configuration of the sample analyzer 1.

The sample analyzer 1 includes a measurement unit 2 and an information processing unit 3.

The measurement unit 2 includes the dispensing part 30 shown in FIG. 2, a detection section 201, a sensor section 202, and a mechanism section 203. The detection section 201 includes the light-emitters 512a and the light-receivers 513a. The sensor section 202 includes sensors for detecting sample containers S and reagent containers R set in the sample container setting section 10 and the reagent holding section 20, the sensor for detecting whether the cover 1b is closed, and the bar code reader 60. The mechanism section 203 includes the lock mechanism 1d, and other mechanisms in the sample analyzer 1.

The information processing unit 3 includes a CPU 301, a ROM 302, a RAM 303, a hard disk 304, an I/O interface 305, and the output section 1a shown in FIG. 1.

The CPU 301 executes computer programs stored in the ROM 302 and computer programs loaded onto the RAM 303. The RAM 303 is used for reading out computer programs stored in the ROM 302 and the hard disk 304. The RAM 303 is also used as work area for the CPU 301 when the CPU 301 executes these computer programs.

In the hard disk 304, various computer programs, such as an operating system and application programs, to be executed by the CPU 301, and data used for execution of the computer programs are stored. Moreover, a computer program 306 which causes the CPU 301 to operate as described later is also stored in the hard disk 304.

In the hard disk 304, information regarding necessity/unnecessity of sample analysis for each analysis item for one sample (hereinafter, referred to as "sample analysis order information"), and information regarding reagent containers R that are set (hereinafter, referred to as "reagent information") are stored.

The output section 1a is a display of a touch panel type, and receives an input from the user and presents information to the user by displaying an image. The I/O interface 305 is connected to the CPU 301, the output section 1a, and components of the measurement unit 2. The CPU 301 receives signals from these mechanisms connected to the I/O interface 305, and controls these mechanisms.

<Operation Performed by Sample Analyzer 1>

Hereinafter, operation performed by the sample analyzer 1 will be described.

Figure 5:
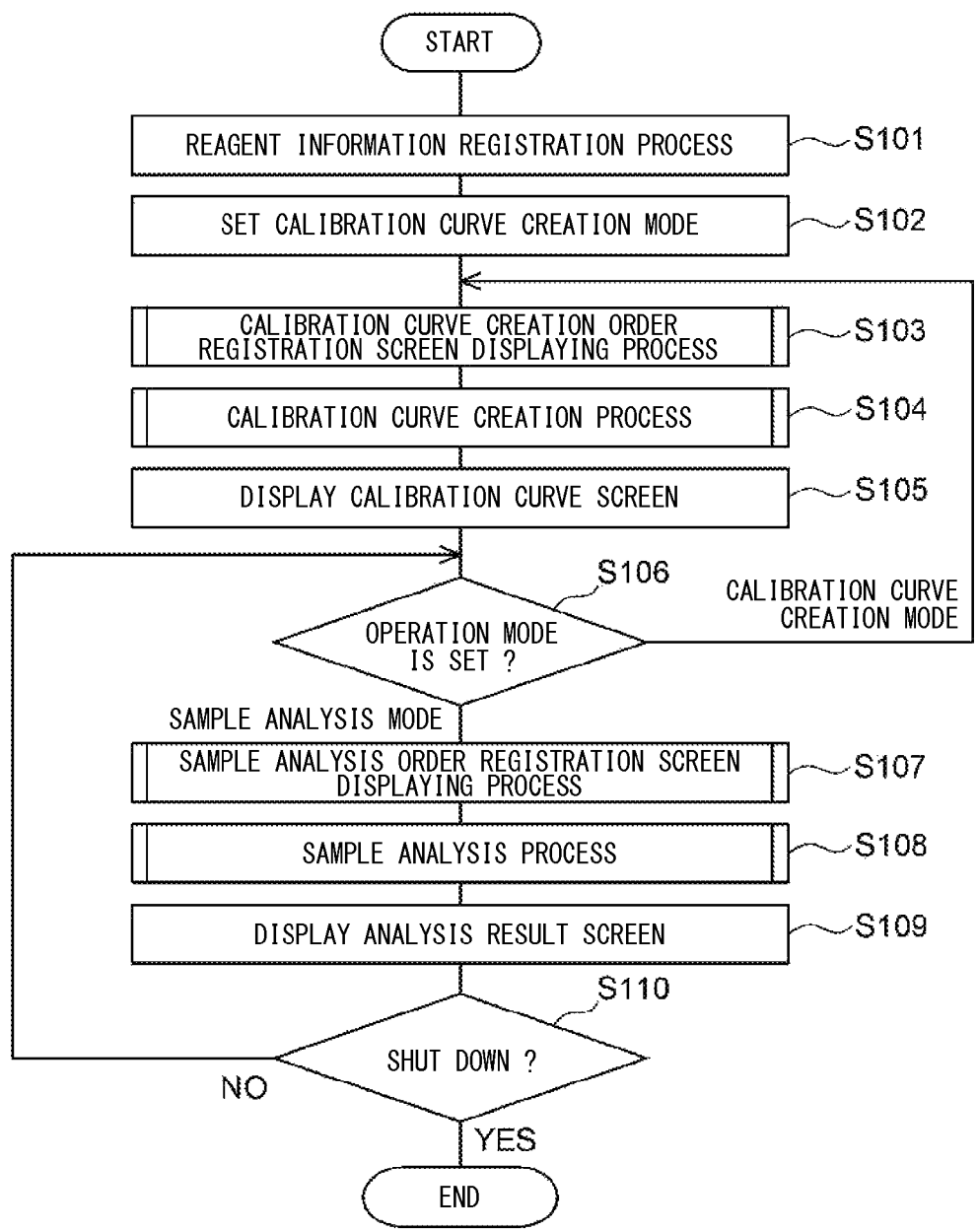
FIG. 5 is a flow chart showing a procedure of operation performed by the sample analyzer according to the embodiment.

FIG. 5 is a flow chart showing a procedure of operation performed by the sample analyzer 1.

First, when the sample analyzer 1 is activated, the CPU 301 executes a reagent information registration process (step S101). When starting use of the sample analyzer 1, the user sets reagents preserved in a freezer, in the reagent holding section 20. There are cases where such a reagent was opened and used in the sample analyzer 1 in the past (for example, on the preceding day), and where the reagent is newly opened. In a case where the reagent was used in the sample analyzer 1 in the past, reagent information including a reagent code of the reagent and a remaining number of tests as a measurable number of times is stored in the hard disk 304. In the reagent information registration process, the user uses the bar code reader 60 to read out a bar code of a bar code label attached to a case or the like of each reagent. In the sample analyzer 1, a CK19 primer reagent, a beta actin primer reagent, and an enzyme reagent are provided as a kit, and the CK19 primer reagent, the beta actin primer reagent, and the enzyme reagent contained in one kit are used in combination. For example, a CK19 primer reagent and an enzyme reagent that are not included in one kit are not used in combination. Moreover, one reagent bar code is allocated to one kit, and reagent information of one set of a CK19 primer reagent, a beta actin primer reagent, and an enzyme reagent is registered by using one bar code.

The bar code includes a reagent code individually allocated to each reagent kit, and the reagent code read out by the bar code reader 60 is provided to the CPU 301. This reagent code includes information of a lot number, an expiration date, the remaining numbers of tests, and the like of the reagents. The CPU 301 checks the read out reagent code against reagent codes stored in the hard disk 304, and determines whether the reagents were used in the past. In a case where the reagents were used in the past, reagent information including the reagent code and the remaining numbers of tests is read out from the hard disk 304. In a case where the reagents were not used in the past, initial values of remaining numbers of tests contained in a reagent code are allocated to the reagent code.

When the reagent code is read out, a reagent registration dialogue is displayed in the output section 1a. FIG. 6 shows the reagent registration dialogue. In this reagent registration dialogue D1, a reagent code, a lot number, an expiration date, and the like are displayed. Remaining numbers of tests of the CK19 primer reagent and the enzyme reagent are respectively displayed, and buttons for correcting the respective remaining numbers of tests are also displayed. By selecting a button, the user can correct a remaining number of tests.

The reagent dialogue D1 includes an OK button and a cancel button. When the user selects the OK button, the reagent information being displayed in the reagent dialogue D1 is stored in the hard disk 304, as reagent information of the reagents being used. When the cancel button is selected, the reagent information being displayed in the reagent dialogue D1 is discarded. In this manner, registration of reagent information is performed.

The user opens the cover 1b and sets reagent containers R containing the reagents whose reagent information has been registered, in the holding holes 21 of the reagent holding section 20. When the reagent information has been registered and each reagent container R is set in the reagent holding section 20, the operation mode of the sample analyzer 1 is set to a calibration curve creation mode (step S102). For the sample analyzer 1, the calibration curve creation mode being an operation mode for creating a calibration curve, or a sample analysis mode being an operation mode for performing analysis of a sample can be selectively set. Immediately after activation of the sample analyzer 1, the calibration curve creation mode is set.

Figure 7:
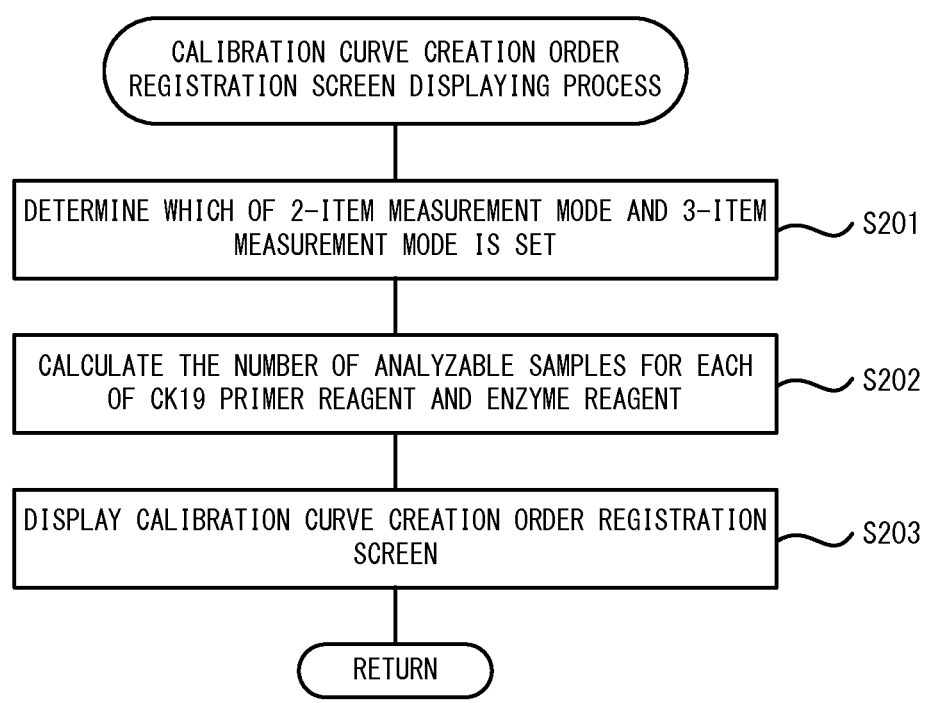
FIG. 7 is a flow chart showing a procedure of a calibration curve creation order registration screen displaying process.

Next, the CPU 301 performs a calibration curve creation order registration screen displaying process (step S103). FIG. 7 is a flow chart showing a procedure of the calibration curve creation order registration screen displaying process.

In the calibration curve creation order registration screen displaying process, the CPU 301 first determines whether the operation mode of the sample analyzer 1 is set to a 2-item measurement mode or a 3-item measurement mode (step S201). Here, the 2-item measurement mode and the 3-item measurement mode will be described. The 2-item measurement mode is a measurement mode for performing analysis of a sample for a CK19 item and a CK19D item. The 3-item measurement mode is a measurement mode for performing analysis of a sample for the CK19 item, the CK19D item, and a beta actin item. Here, the CK19 item is an analysis item for detecting CK19, by measuring a measurement specimen prepared by mixing a normal sample which is not diluted, the CK19 reagent, and the enzyme reagent together. The CK19D item is an analysis item for detecting CK19, by measuring a measurement specimen prepared by mixing a diluted sample, the CK19 reagent, and the enzyme reagent together. The beta actin item is an analysis item for detecting beta actin, by measuring a measurement specimen prepared by mixing a normal sample which is not diluted, the beta actin reagent, and the enzyme reagent together. In the sample analyzer 1, either one operation mode of the 2-item measurement mode and the 3-item measurement mode can be selectively set.

Figure 8:
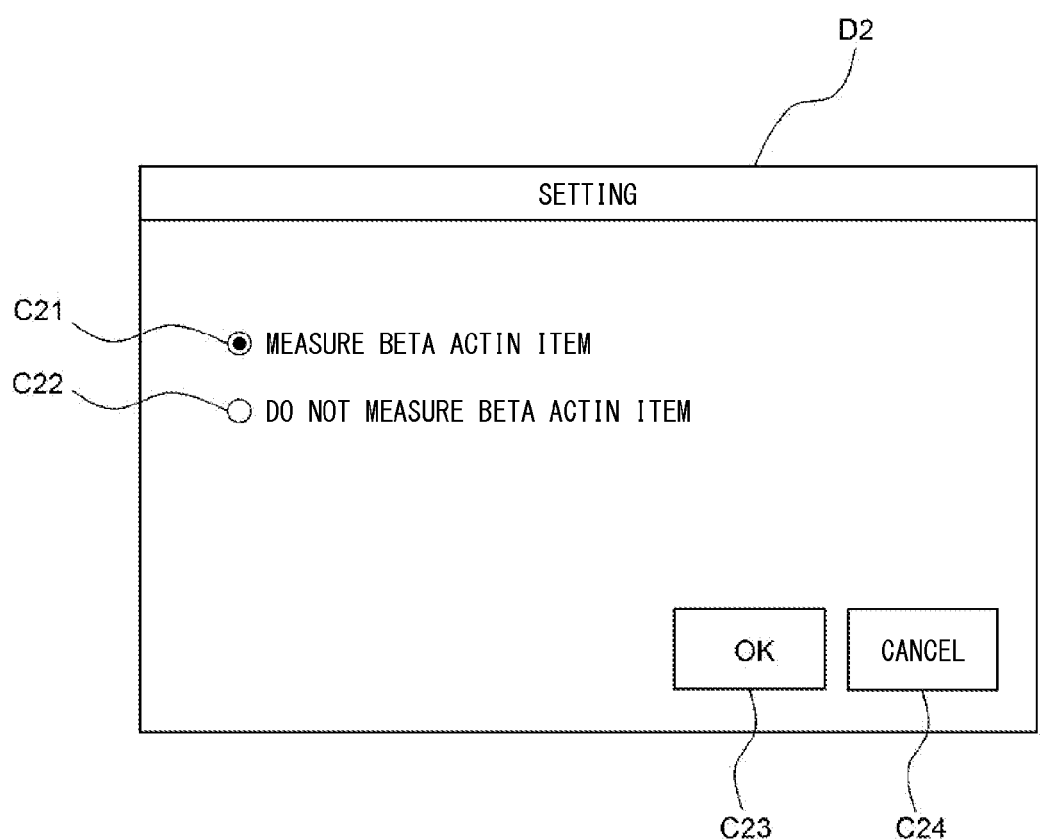
FIG. 8 shows a mode setting screen.

Setting of the 2-item measurement mode or the 3-item measurement mode is performed on a mode setting screen. FIG. 8 shows the mode setting screen. As shown in FIG. 8, a mode setting screen D2 is provided with a radio button C21 for setting the 3-item measurement mode in which the beta actin item is measured, and a radio button C22 for setting the 2-item measurement mode in which the beta actin item is not measured. The user selects either one of the radio buttons C21 and C22, to select either one of the 2-item measurement mode and the 3-item measurement mode. The mode setting screen D2 is further provided with an OK button C23 and a cancel button C24. When the user selects the OK button C23, either one of the 2-item measurement mode and the 3-item measurement mode selected by the radio button C21 or C22 is set. When the cancel button C24 is selected, information of the measurement mode selected on the mode setting screen D2 is discarded, and the setting of the measurement mode before the mode setting screen D2 was displayed is maintained.

The CPU 301 determines which of the 2-item measurement mode and the 3-item measurement mode is set for the sample analyzer 1, and then calculates the number of analyzable samples corresponding to the set measurement mode, for each of the CK19 primer reagent and the enzyme reagent (step S202).

Here, the process of step S202 is described in detail. In step S202, the number of analyzable samples rSC when calibration curve creation is performed is calculated by use of formula (1) or (2) below.

$$rSC = (rT - cT - kT)/s1T \qquad (1)$$

$$rSC = ((rT - kT)/\mathrm{max}1T) \times \mathrm{max}1S + ((rT - kT) \bmod \mathrm{max}1T) - cT\}/s1T \qquad (2)$$

where rT represents a remaining number of tests of a reagent, s1T represents the number of tests of the reagent required for analyzing one sample, cT represents the number of tests of the reagent required for measuring a control, max1T represents a maximum number of tests of the reagent required for analyzing one batch of samples, max1S represents a maximum number of samples included in one batch, kT represents the number of tests of the reagent used for creating a calibration curve. The division is performed using integer division, and when the dividend is not evenly divisible, the fraction less than 1 is truncated, to make an integer. The respective values of rT, s1T, cT, max1T, max1S, and kT are stored in the hard disk 304 in advance.

Here, a batch is described. In the sample container setting section 10 of the sample analyzer 1, a maximum of 14 sample containers S each containing a sample can be set, and further, two sample containers respectively containing a positive control (quality control sample to be used for positive quality control) and a negative control (quality control sample to be used for negative quality control) can be set. In such a state where a plurality of samples and controls are set in the sample container setting section 10, when an instruction to start measurement is given to the sample analyzer 1, measurement of the plurality of samples and controls set in the sample container setting section 10 is continuously performed. In the present embodiment, such a plurality of samples and controls which are set in the sample container setting section 10 and which are to be continuously measured are referred to as a batch. In a case where sample analysis of one batch is performed, two types of controls are always measured, and positive quality control and negative quality control are performed.

In a case where the 2-item measurement mode is set, a maximum of seven samples (seven normal samples and seven diluted samples) can be set in the sample container setting section 10. That is, the maximum number of samples that can be measured for one batch is 7. In order to analyze one sample, measurement of a normal sample and measurement of a diluted sample are needed to be performed. Therefore, an amount of the CK19 primer reagent corresponding to 2 tests and an amount of the enzyme reagent corresponding to 2 tests are used in analysis of one sample. Moreover, always two quality control samples are included in one batch. Thus, an amount of the CK19 primer reagent corresponding to 2 tests and an amount of the enzyme reagent corresponding to 2 tests are used in quality control of one batch. Therefore, the maximum number of tests of the CK19 primer reagent to be used in sample analysis of one batch is 7×2+2=16, and the maximum number of tests of the enzyme reagent to be used in sample analysis of one batch is also 16.

In a case where the 3-item measurement mode is set, a maximum of four samples (four normal samples for CK19 measurement and beta actin measurement, and four diluted samples for CK19D measurement) can be set in the sample container setting section 10. That is, the maximum number of samples that can be measured for one batch is 4. In order to analyze one sample, measurement of CK19 using a normal sample, measurement of CK19D using a diluted sample, and measurement of beta actin using a normal sample need to be performed. Therefore, an amount of the CK19 primer reagent corresponding to 2 tests, an amount of the beta actin primer reagent corresponding to 1 test, and an amount of the enzyme reagent corresponding to 3 tests are used in analysis of one sample. Moreover, always two quality control samples are included in one batch. Thus, for quality control of one batch in the 3-item measurement mode, a total of 4 measurements, i.e., positive quality control and negative quality control for CK19, positive quality control and negative quality control for beta actin are performed. That is, in quality control of one batch in the 3-item measurement mode, an amount of the CK19 primer reagent corresponding to 2 tests, an amount of the beta actin primer reagent corresponding to 2 tests, and an amount of the enzyme reagent corresponding to 4 tests are used. Therefore, the maximum number of tests of the CK19 primer reagent to be used in sample analysis of one batch is 4×2+2=10, and the maximum number of tests of the enzyme reagent to be used in sample analysis of one batch is 4×3+4=16.

Further, in a case where a calibration curve is created in the 2-item measurement mode, three sample containers respectively containing three calibrators are set in the sample container setting section 10. For calibration curve creation in the 2-item measurement mode, a total of 5 measurements, i.e., measurement of CK19 using three calibrators, measurement of CK19 using two quality control samples (positive quality control sample and negative quality control sample) are necessary. Therefore, in calibration curve creation in the 2-item measurement mode, an amount of the CK19 primer reagent corresponding to 5 tests and an amount of the enzyme reagent corresponding to 5 tests are used.

In a case where a calibration curve is created in the 3-item measurement mode, four sample containers respectively containing four calibrators are set in the sample container setting section 10. For calibration curve creation in the 3-item measurement mode, measurement of CK19 using three calibrators, measurement of beta actin using one calibrator, measurement of CK19 using two quality control samples (positive quality control sample and negative quality control sample) and measurement of beta actin using two quality control samples (positive quality control sample and negative quality control sample) are necessary. Therefore, for calibration curve creation in the 3-item measurement mode, an amount of the CK19 primer reagent corresponding to 5 tests, an amount of the beta actin primer reagent corresponding to 3 tests, and an amount of the enzyme reagent corresponding to 8 tests are used.

In a case where the 2-item measurement mode is set, when the remaining number of tests of the CK19 primer reagent is less than 21, which is a result of adding 5 (tests) to be used in calibration curve creation to 16 being the maximum number of tests of the reagent to be used in sample analysis of one batch, then, in step S202, formula (1) is used to calculate the number of analyzable samples rSC of the CK19 primer reagent. When the remaining number of tests of the CK19 primer reagent is not less than 21, then, in step S202, formula (2) is used to calculate the number of analyzable samples rSC of the CK19 primer reagent. In a case where the 2-item measurement mode is set, also when the number of analyzable samples rSC of the enzyme reagent is to be calculated, if the remaining number of tests of the enzyme reagent is less than 21, then, formula (1) is use and, and if the remaining number of tests of the enzyme reagent is not less than 21, formula (2) is used.

On the other hand, in a case where the 3-item measurement mode is set, when the remaining number of tests of the CK19 primer reagent is less than 15, which is a result of adding 5 (tests) to be used in calibration curve creation to 10 being the maximum number of tests of the CK19 primer reagent to be used in sample analysis of one batch, then, in step S202, formula (1) is used to calculate the number of analyzable samples rSC of the CK19 primer reagent. When the remaining number of tests of the CK19 primer reagent is not less than 15, then, in step S202, formula (2) is used to calculate the number of analyzable samples rSC of the CK19 primer reagent. Further, in a case where the 3-item measurement mode is set, when the remaining number of tests of the enzyme reagent is less than 24, which is a result of adding 8 (tests) to be used in calibration curve creation to 16 being the maximum number of tests of the enzyme reagent to be used in sample analysis of one batch, then, in step S202, formula (1) is used to calculate the number of analyzable samples rSC of the enzyme reagent. When the remaining number of tests of the enzyme reagent is not less than 24, then, in step S202, formula (2) is used to calculate the number of analyzable samples rSC of the enzyme reagent. It should be noted that in a case where the 3-item measurement mode is set, the reagents to be used in measurement are the CK19 primer reagent, the beta actin primer reagent, and the enzyme reagent, but only for each of the CK19 primer reagent and the enzyme reagent, the number of analyzable samples rSC is calculated. This is because, compared with the CK19 primer reagent and the enzyme reagent, the volume of the beta actin reagent container R is large, and thus, the initial value of the remaining number of tests thereof is large.

Here, as an example, the number of analyzable samples rSC of the CK19 primer reagent when the remaining number of tests of the CK19 primer reagent is 15 in a case where the 2-item measurement mode is set is explained. Since rT is 15 and the 2-item measurement mode is set, s1T is 2, cT is 2, max1T is 16, max1S is 7, and kT is 5. Therefore, when these numerical values are assigned to formula (1), rSC is 4.

As another example, the number of analyzable samples rSC of the CK19 primer reagent when the remaining number of tests of the CK19 primer reagent is 60 in a case where the 2-item measurement mode is set is explained. In this case, rT is 60, and the other parameters are the same as those in the above example. Therefore, when the numerical values are assigned to formula (2), rSC is 23.

As described above, since the number of analyzable samples is calculated in consideration of measurement using calibrators and controls which are different from samples collected from subjects, an accurate number of analyzable samples can be obtained.

When the process of step S202 as described above ends, the CPU 301 causes the output section 1a to display a calibration curve creation order registration screen (step S203). FIG. 9A shows the calibration curve creation order registration screen in the 2-item measurement mode. As shown in FIG. 9A, a calibration curve creation order registration screen D31 includes a region A311 for displaying information regarding reagents, a region A312 for displaying information regarding controls to be used in calibration curve creation, and a region A313 for displaying measurement order information of calibrators as information of request for calibration curve creation.

In the region A311, information regarding reagents such as a lot number, an expiration date, an expiration date after opening, and the like; the number of analyzable samples S311 of the CK19 primer reagent in the 2-item measurement mode; and the number of analyzable samples S312 of the enzyme reagent in the 2-item measurement mode are displayed.

In the region A312, information of holding holes, in the sample container setting section 10, being positions where controls are set, and the names of the controls are displayed. In the region A312, two display lines are provided, and each line corresponds to a position in the sample container setting section 10. In each line of the region A312, the name of a corresponding control is displayed. Moreover, in the region A312, the same information is always displayed in a fixed manner, and the user cannot edit or change the displayed information.

In the region A313, information of holding holes, in the sample container setting section 10, being positions where calibrators are set, and the names of the calibrators are displayed. In the region A313, three display lines are provided, and each line corresponds to a position in the sample container setting section 10. In each line of the region A313, information of a corresponding calibrator is displayed. Moreover, in the region A313, in the initial state, no information of calibrators is displayed. The user performs a predetermined operation on the calibration curve creation order registration screen D31, thereby being able to register information of calibrators to be used in calibration curve creation, as measurement order information representing a request for calibration curve creation. When the measurement order information of the calibrators has been registered by the user, the measurement order information is displayed in the region A313.

In the calibration curve creation order registration screen D31, a start button C35 for giving an instruction to start measurement is also provided. The start button C35 is selectable by the user operating the output section 1a. By the start button C35 being selected, an instruction to start measurement is given to the CPU 301.

In the calibration curve creation order registration screen D31, a list box C36 for setting an operation mode is further provided. The list box C36 has a choice of the calibration curve creation mode and a choice of the sample analysis mode. The user can set the operation mode to either one of the calibration curve creation mode and the sample analysis mode, by operating the list box C36. The choice of the calibration curve creation mode includes a character string "Calibrator", and the choice of the sample analysis mode includes a character string "Sample" (see FIG. 13A, FIG. 13B). The calibration curve creation order registration screen D31 is in a state where the calibration curve creation mode is selected in the list box C36. When the sample analysis mode is selected in the list box C36, the operation mode is changed to the sample analysis mode, and the display in the output section 1a changes from the calibration curve creation order registration screen D31 to a sample analysis order registration screen described later.

FIG. 9B shows the calibration curve creation order registration screen in the 3-item measurement mode. As shown in FIG. 9B, a calibration curve creation order registration screen D32 in the 3-item measurement mode includes a region A321 for displaying information regarding reagents, a region A322 for displaying information regarding controls to be used in calibration curve creation, and a region A323 for displaying measurement order information of the calibrators.

In the region A321, the number of analyzable samples S321 of the CK19 primer reagent in the 3-item measurement mode, and the number of analyzable samples S322 of the enzyme reagent in the 3-item measurement mode are displayed.

In the region A322, information of holding holes, in the sample container setting section 10, being positions where controls are set, and the names of the controls are displayed. In the region A322, three display lines are provided, and each line corresponds to a position in the sample container setting section 10. In each line of the region A322, the name of a corresponding control is displayed. The other features are the same as those of the region A312 on the calibration curve creation order registration screen D31 in the 2-item measurement mode, and thus, description thereof will be omitted.

In the region A323, information of holding holes, in the sample container setting section 10, being positions where calibrators are set, and the names of the calibrators are displayed. In the region A323, four display lines are provided, and each line corresponds to a position in the sample container setting section 10. In each line of the region A323, the name of a corresponding calibrator is displayed. The other features are the same as those of the region A313 on the calibration curve creation order registration screen D31 in the 2-item measurement mode, and thus, description thereof will be omitted.

In the calibration curve creation order registration screen D32, the start button C35 for giving an instruction to start measurement, and the list box C36 for setting an operation mode are further provided. These are also the same as the start button C35 and the list box C36 on the calibration curve creation order registration screen D31 in the 2-item measurement mode.

When the calibration curve creation order registration screen D31, D32 as described above is displayed, the CPU 301 returns the processing to the main routine.

The user can confirm the number of analyzable samples S311, S321 of the CK19 primer reagent and the number of analyzable samples S312, S322 of the enzyme reagent on the calibration curve creation order registration screen D31, D32, to determine whether to create a calibration curve. For example, in a case where the number of analyzable samples S311 or S312 (S321 or S322) is 0 or a very small number greater than or equal to 1, even if a calibration curve is created, sample analysis cannot be performed, or only a small number of samples can be analyzed. In such a case, the user can replace the reagent with a new one, without performing creation of a calibration curve. Accordingly, time taken for measurement for creating a calibration curve can be cut, and consumption of the calibrators and the controls can be suppressed.

Figure 10:
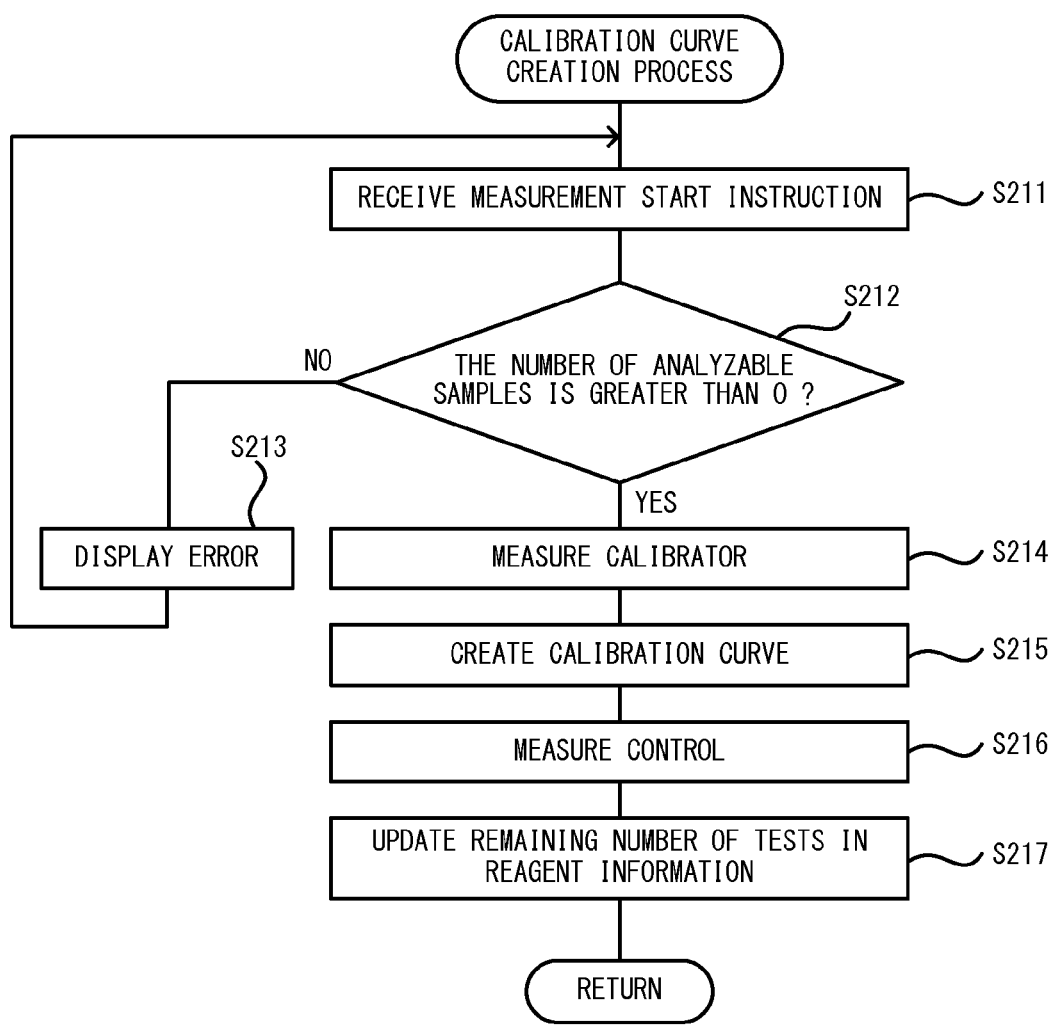
FIG. 10 is a flow chart showing a procedure of a calibration curve creation process.

Next, the CPU 301 performs a calibration curve creation process (step S104). FIG. 10 is a flow chart showing a procedure of the calibration curve creation process.

In the sample analyzer 1, in order to realize highly-accurate sample analysis by eliminating influence of preservation of the reagents in a freezer, after the power is turned on and the sample analyzer 1 is activated, calibration curve creation is performed prior to sample analysis. When performing calibration curve creation, the user sets a sample container S containing a positive control and a sample container S containing a negative control in predetermined holding holes 11 in the sample container setting section 10, sets three sample containers S respectively containing calibrators in predetermined holding holes 11 in the sample container setting section 10, and sets reaction containers M in predetermined reaction container setting parts 511 in the measurement section 50. Further, the user registers measurement order information of the calibrators on the calibration curve creation order registration screen D31, D32, and selects the start button C35 to input a measurement start instruction (step S211).

Upon receiving the measurement start instruction, the CPU 301 determines whether the number of analyzable samples of the CK19 primer reagent and the number of analyzable samples of the enzyme reagent obtained as described above are greater than 0 (step S212). When either one of the number of analyzable samples of the CK19 primer reagent and the number of analyzable samples of the enzyme reagent is 0 (NO in step S212), the CPU 301 does not perform measurement of the calibrators and causes the output section 1a to display an error screen (step S213).

Figure 11:
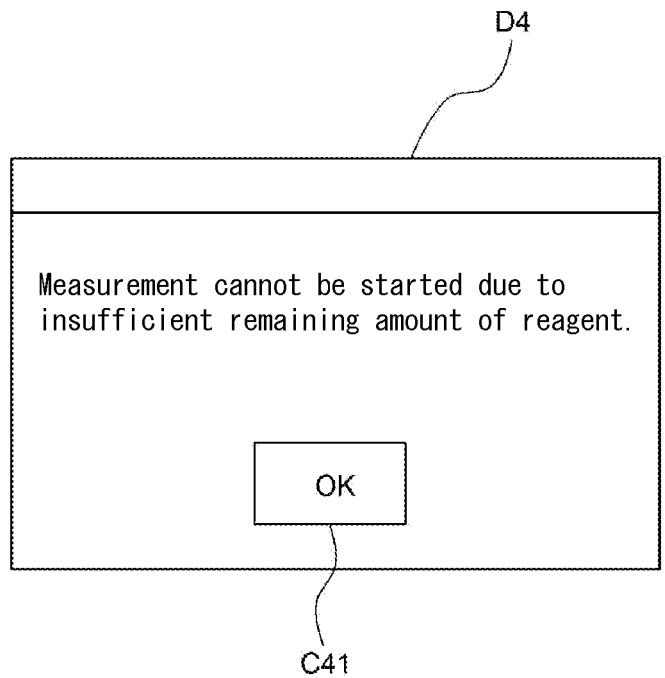
FIG. 11 shows an error screen.

FIG. 11 shows the error screen. As shown in FIG. 11, on an error screen D4, character information "Measurement cannot be started due to insufficient remaining amount of reagent." is displayed. The error screen D4 is also provided with an OK button C41. The user can close the error screen D4 by selecting the OK button C41.

After the error screen D4 is closed, the CPU 301 returns the processing to step S211. Accordingly, the user can replace the reagent with a new one and give an instruction of calibration curve creation.

In step S212, when the number of analyzable samples of the CK19 primer reagent and the number of analyzable samples of the enzyme reagent are greater than 0 (YES in step S212), first, measurement of three calibrators is performed (step S214). In the following, operation of measuring calibrators will be described, for each of the 2-item measurement mode, and the 3-item measurement mode, separately.

<Calibrator Measurement Operation in 2-Item Measurement Mode>

In calibration curve creation when the 2-item measurement mode is set, the CK19 primer reagent is aspirated from its reagent container R and discharged into receptacles M12 of reaction containers M. Specifically, the CK19 primer reagent is discharged into each of the left and right receptacles M12 of one reaction container M, and the CK19 primer reagent is discharged into either one of the left and right receptacles M12 of another reaction container M. That is, the CK19 primer reagent is consumed by an amount corresponding to 3 tests.

Subsequently, from the three sample containers S respectively containing calibrators, the calibrators are aspirated respectively and discharged into the three receptacles M12 in which the CK19 primer reagent has been discharged, respectively. Further, the enzyme reagent is aspirated from its reagent container R, and is discharged into the three receptacles M12 into which the calibrators have been respectively discharged. That is, the enzyme reagent is consumed by an amount corresponding to 3 tests.

It should be noted that when aspiration is performed, the arm part 31 is moved in the front-rear and left-right directions to determine an aspiration position, and then each syringe part 31a is moved downwardly, whereby the lower end of the pipette tip C attached to a corresponding nozzle part 31b is inserted into a sample container S or a reagent container R. In this state, the pump part is driven, whereby aspiration is performed. When discharge is performed, the arm part 31 is moved in the front-rear and left-right directions to determine a discharge position, and then each syringe part 31a is moved downwardly, whereby the lower end of the pipette tip C attached to a corresponding nozzle part 31b is inserted into a receptacle M12 of a reaction container M. In this state, the pump part is driven, whereby discharge is performed.

Next, the reaction container M for which the discharge has been performed is closed tight by the caps being closed by means of the cap holding member 515 of the measurement section 50. In this state, the inside of the reaction container M is heated to about 20 to 65° C. by a Peltier module (not shown) arranged below the reaction container setting part 511. Then, as described above, light emitted from each light-emitter 512a transmits through a corresponding receptacle M12 of the reaction container M to be received by a corresponding light-receiver 513a. At this time, based on a detection signal from the light-receiver 513a, turbidity inside the receptacle M12 during nucleic acid amplification reaction is obtained in real time. Then, measurement of the calibrators ends.

<Calibrator Measurement Operation in 3-Item Measurement Mode>

In calibration curve creation when the 3-item measurement mode is set, as in the case of the 2-item measurement mode, the CK19 primer reagent is aspirated from its reagent container R and discharged into receptacles M12 of reaction containers M. Specifically, the CK19 primer reagent is discharged into each of the left and right receptacles M12 of one reaction container M, and the CK19 primer reagent is discharged into either one of the left and right receptacles M12 of another reaction container M. That is, the CK19 primer reagent is consumed by an amount corresponding to 3 tests.

Next, in the 3-item measurement mode, the beta actin primer reagent is aspirated from its reagent container R, and discharged into a receptacle M12 different from the receptacle M12 of the reaction container M into which the CK19 primer reagent has been dispensed. Specifically, the beta actin primer reagent is discharged into one receptacle M12 of the reaction container M having the other receptacle M12 into which the CK19 primer reagent has been discharged.

Subsequently, calibrators are respectively aspirated from the four sample containers S respectively containing calibrators, and discharged into the three receptacles M12 into which the CK19 primer reagent has been discharged and the one receptacle M12 into which the beta actin primer reagent has been discharged. Further, the enzyme reagent is aspirated from its reagent container R and discharged into the four receptacles M12 into which the calibrators have been discharged. That is, the enzyme reagent is consumed by an amount corresponding to 4 tests.

Next, each reaction container M for which the discharge has been performed is closed tight by the caps being closed by means of the cap holding member 515 of the measurement section 50. In this state, the inside of the reaction container M is heated to about 20 to 65° C. by a Peltier module (not shown) arranged below the reaction container setting part 511. Then, as described above, light emitted from each light-emitter 512a transmits through a corresponding receptacle M12 of the reaction container M to be received by a corresponding light-receiver 513a. At this time, based on a detection signal from the light-receiver 513a, turbidity inside the receptacle M12 during nucleic acid amplification reaction is generated in real time. Then, measurement of the calibrators ends.

Upon completion of the measurement of the calibrators, based on the generated turbidities and measurement values of the calibrators provided in advance, a calibration curve is created and stored in the hard disk 304 (step S215).

Moreover, in parallel with the above measurement of the three calibrators, measurement of the positive control and the negative control is also performed (step S216). In the following, operation of measuring the controls will be described, for each of the 2-item measurement mode and the 3-item measurement mode, separately.

<Control Measurement Operation in 2-Item Measurement Mode>

In measurement of the positive control and the negative control when the 2-item measurement mode is set, the CK19 primer reagent is aspirated from its reagent container R and discharged into receptacles M12 of a reaction container M. Specifically, the CK19 primer reagent is discharged into each of the left and right receptacles M12 of one reaction container M. That is, the CK19 primer reagent is consumed by an amount corresponding to 2 tests.

Subsequently, from the sample containers S respectively containing the positive control and the negative control, the positive control and the negative control are aspirated respectively, and discharged into the two receptacles M12 into which the CK19 primer reagent has been discharged. Subsequently, the enzyme reagent is aspirated from its reagent container R and discharged into the two receptacles M12 into which the positive control and the negative control have been discharged, respectively. That is, the enzyme reagent is consumed by an amount corresponding to 2 tests.

Next, the reaction container M for which the discharge has been performed is closed tight by the caps being closed by means of the cap holding member 515 of the measurement section 50. In this state, the inside of the reaction container M is heated to about 20 to 65° C. by a Peltier module (not shown) arranged below the reaction container setting part 511. Then, light emitted from each light-emitter 512a transmits through a corresponding receptacle M12 of the reaction container M to be received by a corresponding light-receiver 513a. Based on the generated turbidity and the calibration curve created from the measurement results of the calibrators described above, the concentration of the target gene is obtained from the amplification rise time. Then, measurement of the positive control and the negative control ends.

<Control Measurement Operation in 3-Item Measurement Mode>

In measurement of the positive control and the negative control when the 3-item measurement mode is set, the CK19 primer reagent is aspirated from its reagent container R and discharged into receptacles M12 of reaction containers M. Specifically, the CK19 primer reagent is discharged into each of the left and right receptacles M12 of one reaction container M. That is, the CK19 primer reagent is consumed by an amount corresponding to 2 tests.

Next, in the 3-item measurement mode, the beta actin primer reagent is aspirated from its reagent container R and discharged into the receptacles M12 that are different from the receptacles M12 of the reaction container M into which the CK19 primer reagent has been dispensed. Specifically, the beta actin primer reagent is discharged into the left and right receptacles M12 of another reaction container M into which the CK19 primer reagent has not been discharged. That is, the beta actin primer reagent is consumed by an amount corresponding to 2 tests.

Subsequently, the positive control and the negative control are respectively aspirated from the sample containers S respectively containing the positive control and the negative control. Then, the positive control and the negative control are respectively discharged into the two receptacles M12 into which the CK19 primer reagent has been discharged, and also, the positive control and the negative control are respectively discharged into the other two receptacles M12 into which the beta actin primer reagent has been discharged. Subsequently, the enzyme reagent is aspirated from its reagent container R and discharged into the four receptacles M12 into which the positive control and the negative control have been discharged. That is, the enzyme reagent is consumed by an amount corresponding to 4 tests.

Next, each reaction container M for which the discharge has been performed is closed tight by the caps being closed by the cap holding member 515 of the measurement section 50. In this state, the inside of the reaction container M is heated to about 20 to 65° C. by a Peltier module (not shown) arranged below the reaction container setting part 511. Then, light emitted from each light-emitter 512a transmits through a corresponding receptacle M12 of the reaction container M to be received by a corresponding light-receiver 513a. Based on the generated turbidity and the calibration curve created by the measurement results of the calibrators described above, the concentration of the target gene is obtained from the amplification rise time. Then, measurement of the positive control and the negative control ends.

When the measurement of the calibrators and the measurement of the controls as described above have ended, the number of tests of the reagents used in these measurements (5 tests for the CK19 primer reagent in the 2-item measurement mode, 5 tests for the enzyme reagent in the 2-item measurement mode, 5 tests for the CK19 primer reagent in the 3-item measurement mode, 8 tests for the enzyme reagent in the 3-item measurement mode) is subtracted from the remaining number of tests in the reagent information (step S217). Upon update of the remaining number of tests in the reagent information, the CPU 301 returns the processing to the main routine.

When the calibration curve creation process has ended, the CPU 301 causes the output section 1a to display a calibration curve screen (step S105). On the calibration curve screen, the created calibration curve is displayed in the form of a graph, and the user can input an approval of the calibration curve.

Next, the CPU 301 determines whether an operation mode has been set (step S106). After the calibration curve creation described above has been completed, the calibration curve creation mode is automatically changed into the sample analysis mode. Further, by operating the list box C36 described above, the user can select either one of the calibration curve creation mode and the sample analysis mode.

Figure 12:
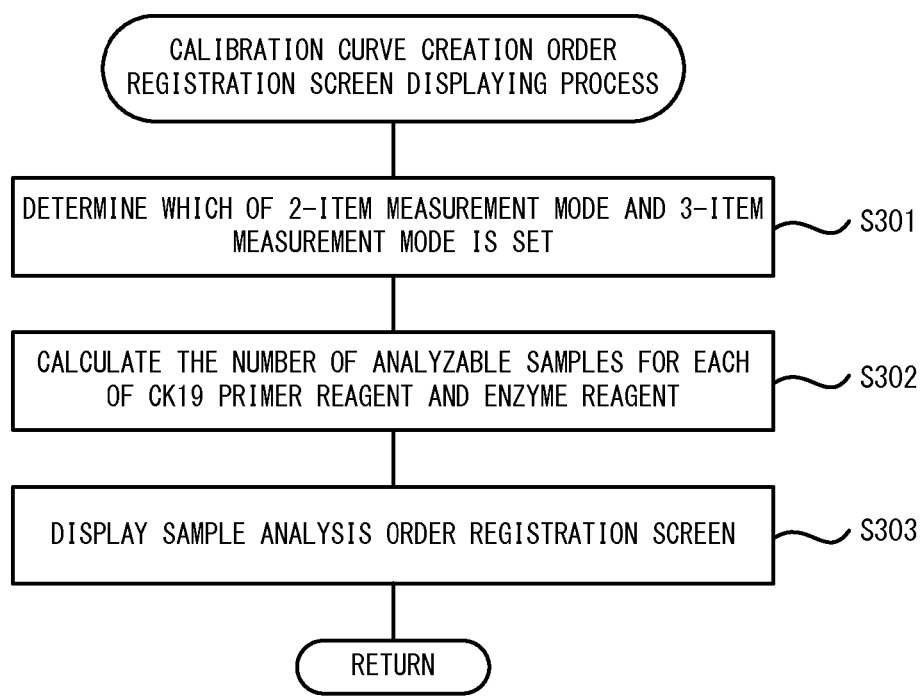
FIG. 12 is a flow chart showing a procedure of a sample analysis order registration screen displaying process.

In step S106, in a case where the operation mode has been set to the sample analysis mode ("the sample analysis mode" in step S106), the CPU 301 performs a sample analysis order registration screen displaying process (step S107). FIG. 12 is a flow chart showing a procedure of the sample analysis order registration screen displaying process.

In the sample analysis order registration screen displaying process, first, the CPU 301 determines which of the 2-item measurement mode and the 3-item measurement mode is set for the sample analyzer 1 (step S301).

After determining which of the 2-item measurement mode and the 3-item measurement mode is set for the sample analyzer 1, the CPU 301 calculates the number of analyzable samples corresponding to the set measurement mode for each of the CK19 primer reagent and the enzyme reagent (step S302).

Here, the process of step S302 is described in detail. In step S302, the number of analyzable samples rSS when sample analysis is performed is calculated by use of formula (3) or (4) below.

$$rSS=(rT-cT)/s1T \qquad (3)$$

$$rSS=(rT/\max 1T)\times \max 1S+(rT \bmod \max 1T)-cT\}/s1T \qquad (4)$$

In a case where the 2-item measurement mode is set, when the remaining number of tests of the CK19 primer reagent is less than 16 which is the maximum number of tests of the reagent to be used in sample analysis of one batch, then, in step S302, formula (3) is used to calculate the number of analyzable samples rSS of the CK19 primer reagent. When the remaining number of tests of the CK19 primer reagent is not less than 16, then, in step S302, formula (4) is used to calculate the number of analyzable samples rSS of the CK19 primer reagent. Also in a case where the 2-item measurement mode is set and the number of analyzable samples rSS of the enzyme reagent is to be calculated, when the remaining number of tests of the enzyme reagent is less than 16, formula (3) is used, and when the remaining number of tests of the enzyme reagent is not less than 16, formula (4) is used.

On the other hand, in a case where the 3-item measurement mode is set, when the remaining number of tests of the CK19 primer reagent is less than 10 which is the maximum number of tests of the CK19 primer reagent to be used in sample analysis of one batch, then, in step S302, formula (3) is used to calculate the number of analyzable samples rSS of the CK19 primer reagent. When the remaining number of tests of the CK19 primer reagent is not less than 10, then, in step S302, formula (4) is used to calculate the number of analyzable samples rSS of the CK19 primer reagent. Further, in a case where the 3-item measurement mode is set, when the remaining number of tests of the enzyme reagent is less than 16 which is the maximum number of tests of the enzyme reagent to be used in sample analysis of one batch, then, in step S302, formula (3) is used to calculate the number of analyzable samples rSS of the enzyme reagent. When the remaining number of tests of the enzyme reagent is not less than 16, then, in step S302, formula (4) is used to calculate the number of analyzable samples rSS of the enzyme reagent. It should be noted that in a case where the 3-item measurement mode is set, the reagents to be used in measurement are the CK19 primer reagent, the beta actin primer reagent, and the enzyme reagent, but only for each of the CK19 primer reagent and the enzyme reagent, the number of analyzable samples rSS is calculated.

Here, as an example, the number of analyzable samples rSS of the CK19 primer reagent when the remaining number of tests of the CK19 primer reagent is 15 in a case where the 2-item measurement mode is set is explained. Since rT is 15 and the 2-item measurement mode is set, s1T is 2, cT is 2, max1T is 16, and max1S is 7. Therefore, when these numerical values are assigned to formula (3), rSS is 6.

As another example, the number of analyzable samples rSS of the CK19 primer reagent when the remaining number of tests of the CK19 primer reagent is 60 in a case where the 2-item measurement mode is set is explained. In this case, rT is 60, and the other parameters are the same as those in the above example. Therefore, when the numerical values are assigned to formula (4), rSS is 26.

As described above, since the number of analyzable samples is calculated in consideration of measurements using controls which are different from samples collected from subjects, an accurate number of analyzable samples can be obtained.

When the process of step S302 as described above ends, the CPU 301 causes the output section 1*a* to display the sample analysis order registration screen (step S303). FIG. 13A shows the sample analysis order registration screen in the 2-item measurement mode. As shown in FIG. 13A, the sample analysis order registration screen D51 includes a region A511 for displaying information regarding reagents, a region A512 for displaying information regarding controls to be used in sample analysis, and a region A513 for displaying sample analysis order information as information of request for sample analysis.

In the region A511, as in the case of the calibration curve creation order registration screen D31, D32, information regarding reagents such as a lot number, an expiration date, an expiration date after opening, and the like; the number of analyzable samples S511 of the CK19 primer reagent in the 2-item measurement mode; and the number of analyzable samples S512 of the enzyme reagent in the 2-item measurement mode are displayed.

In the region A512, information of holding holes, in the sample container setting section 10, being positions where controls are set, and the names of the controls are displayed. In the region A512, two display lines are provided, and each line corresponds to a position in the sample container setting section 10. In each line of the region A512, the name of a corresponding control is displayed. Moreover, in the region A512, as in the case of the calibration curve creation order registration screen D31, D32, the same information is always displayed in a fixed manner, and the user cannot edit or change the displayed information.

In the region A513, information of holding holes, in the sample container setting section 10, being positions where samples are set, and the sample IDs of the samples are displayed. In the region A513, seven display lines are provided, and each line corresponds to a position in the sample container setting section 10. In each line of the region A513, information of a corresponding sample is displayed. In the region A513, in the initial state, no information of samples is displayed. The user performs a predetermined operation on the sample analysis order registration screen D51, thereby being able to register information of samples to be analyzed, as sample analysis order information. When the sample analysis order information has been registered by the user, the sample analysis order information is displayed in the region A513.

The sample analysis order registration screen D51 is provided with a start button C55 for giving an instruction to start measurement, as in the case of the calibration curve creation order registration screen D31, D32.

The sample analysis order registration screen D51 is further provided with a list box C56 for setting an operation mode, as in the case of the calibration curve creation order registration screen D31, D32. The sample analysis order registration screen D51 is in a state where the sample analysis mode is selected in the list box C56. When the calibration curve creation mode is selected in the list box C56, the operation mode is changed to the calibration curve creation mode, and the display in the output section 1a changes from the sample analysis order registration screen D51 to the calibration curve creation order registration screen D31.

FIG. 13B shows the sample analysis order registration screen in the 3-item measurement mode. As shown in FIG. 13B, the sample analysis order registration screen D52 in the 3-item measurement mode includes a region A521 for displaying information regarding reagents, a region A522 for displaying information regarding controls to be used in sample analysis, and a region A523 for displaying sample analysis order information.

In the region A521, the number of analyzable samples S521 of the CK19 primer reagent in the 3-item measurement mode, and the number of analyzable samples S522 of the enzyme reagent in the 3-item measurement mode are displayed.

In the region A522, information of holding holes, in the sample container setting section 10, being positions where controls are set, and the names of the controls are displayed. In the region A522, three display lines are provided, and each line corresponds to a position in the sample container setting section 10. In each line of the region A522, the name of a corresponding control is displayed. The other features are the same as those of the region A512 on the sample analysis order registration screen D51 in the 2-item measurement mode, and thus, description thereof is omitted.

In the region A523, information of holding holes, in the sample container setting section 10, being positions where samples are set, and the sample IDs of the samples are displayed. In the region A523, four display lines are provided, and each line corresponds to a position in the sample container setting section 10. In each line of the region A523, information of a corresponding sample is displayed. The other features are the same as those of the region A513 on the sample analysis order registration screen D51 in the 2-item measurement mode, and thus, description thereof is omitted.

In the sample analysis order registration screen D52, the start button C55 for giving an instruction to start measurement and the list box C56 for setting an operation mode are further provided. These are also the same as the start button C55 and the list box C56 on the sample analysis order registration screen D51 in the 2-item measurement mode.

When the sample analysis order registration screen D51, D52 as described above is displayed, the CPU 301 returns the processing to the main routine.

The user can confirm the number of analyzable samples S511, S521 of the CK19 primer reagent and the number of analyzable samples S512, S522 of the enzyme reagent on the sample analysis order registration screen D51, D52, to determine whether to perform sample analysis. For example, in a case the number of analyzable samples S511 or S512 is 0 or a very small number greater than or equal to 1, sample analysis cannot be performed, or only a small number of samples can be analyzed. In such a case, the user can replace the reagent with a new one, without performing sample analysis.

Figure 14:
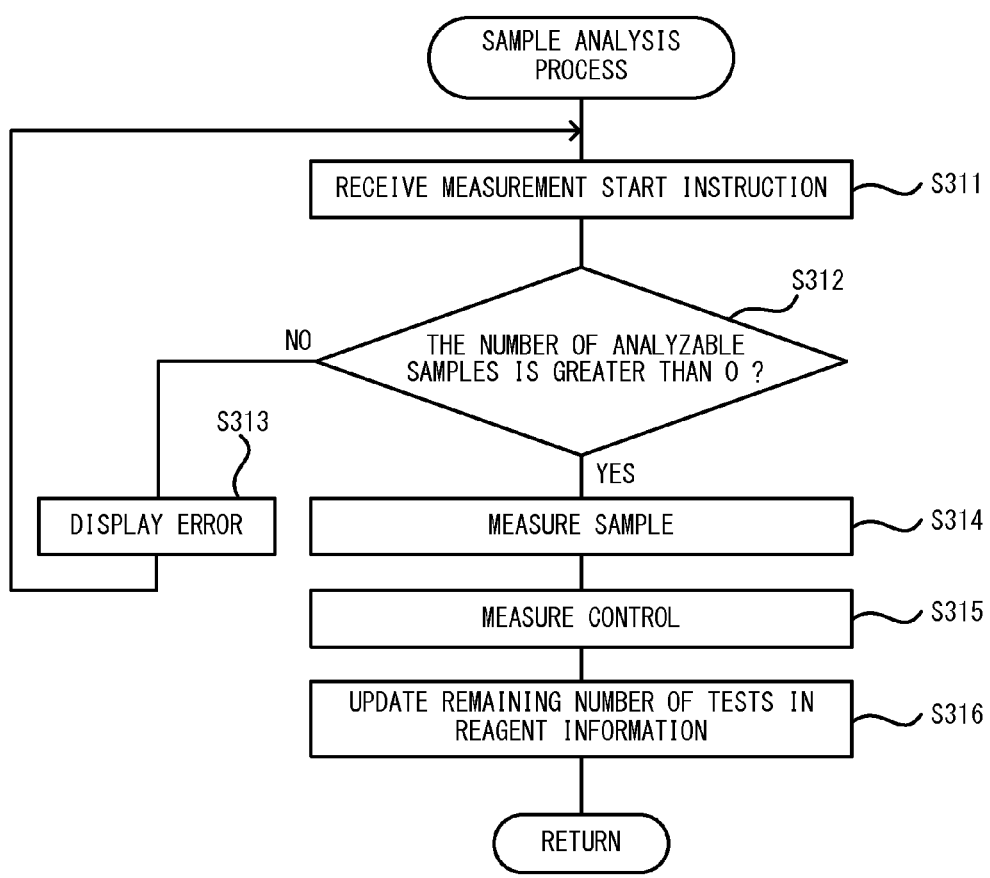
FIG. 14 is a flow chart showing a procedure of a sample analysis process.

In a case where sample analysis is performed, the CPU 301 performs a sample analysis process (step S108). FIG. 14 is a flow chart showing a procedure of the sample analysis process.

When performing sample analysis, the user sets a sample container S containing a positive control and a sample container S containing a negative control in predetermined holding holes 12 in the sample container setting section 10, sets a maximum of seven sample containers S respectively containing normal samples, and a maximum of seven sample containers S respectively containing diluted samples in predetermined holding holes 11 in the sample container setting section 10, and sets reaction containers M in predetermined reaction container setting parts 511 in the measurement section 50. Further, the user registers analysis order information on the sample analysis order registration screen D51, D52 and selects the start button C55 to input an instruction to start measurement (step S311).

Upon receiving the measurement start instruction, the CPU 301 determines whether the number of analyzable samples of the CK19 primer reagent and the number of analyzable samples of the enzyme reagent obtained as described above are greater than 0 (step S312). When either one of the number of analyzable samples of the CK19 primer reagent and the number of analyzable samples of the enzyme reagent is 0 (NO in step S312), the CPU 301 does not perform sample measurement and causes the output section 1a to display the error screen D4 (step S313).

After the OK button is selected (see FIG. 11) and the error screen D4 is closed, the CPU 301 returns the processing to step S311. Accordingly, the user can replace the reagent with a new one and give an instruction to perform sample analysis.

In step S312, when the number of analyzable samples of the CK19 primer reagent and the number of analyzable samples of the enzyme reagent are greater than 0 (YES in step S312), sample measurement is performed, first (step S314). In the following, operation of sample measurement will be described, for each of the 2-item measurement mode and the 3-item measurement mode, separately. In the following, a case where seven samples are analyzed will be described for the 2-item measurement mode, and a case where four samples are analyzed will be described for the 3-item measurement mode.

<Sample Measurement Operation in 2-Item Measurement Mode>

In sample measurement when the 2-item measurement mode is set, the CK19 primer reagent is aspirated from its reagent container R and discharged into receptacles M12 of reaction containers M. Specifically, the CK19 primer reagent is discharged into each of the left and right receptacles M12 of seven reaction containers M. That is, the CK19 primer reagent is consumed by an amount corresponding to 14 tests.

Subsequently, from the 14 sample containers S containing seven normal samples and seven diluted samples, the seven normal samples and the seven diluted samples are respectively aspirated. Then, the normal samples are respectively discharged into the receptacles M12 on one side (for example, left) of the seven reaction containers M into which the CK19 primer reagent has been discharged. The diluted samples are respectively discharged into the receptacles M12 on the other side (for example, right) of the seven reaction containers M into which the CK19 primer reagent has been discharged. Here, a normal sample and a diluted sample prepared from one sample are respectively discharged into the two receptacles M12 of one reaction container M.

Further, the enzyme reagent is aspirated from its reagent container R and discharged into the 14 receptacles M12 into which the samples have been discharged. That is, the enzyme reagent is consumed by an amount corresponding to 14 tests.

Next, each reaction container M for which the discharge has been performed is closed tight by the caps being closed by means of the cap holding member 515 of the measurement section 50. In this state, the inside of the reaction container M is heated to about 20 to 65° C. by a Peltier module (not shown) arranged below the reaction container setting part 511, and nucleic acid of the target gene (mRNA) is amplified through LAMP reaction. Then, as described above, light emitted from each light-emitter 512a transmits through a corresponding receptacle M12 of the reaction container M to be received by a corresponding light-receiver 513a. At this time, based on a detection signal from the light-receiver 513a, turbidity inside the receptacle M12 during nucleic acid amplification reaction is generated in real time. Based on the generated turbidity and the calibration curve created in advance from measurement results of the calibrators, the concentration of the target gene can be obtained from the amplification rise time. Thus, measurement of the samples ends.

<Sample Measurement Operation in 3-Item Measurement Mode>

In sample measurement when the 3-item measurement mode is set, as in the case of the 2-item measurement mode, the CK19 primer reagent is aspirated from its reagent container R and discharged into receptacles M12 of reaction containers M. Specifically, the CK19 primer reagent is discharged into each of eight receptacles M12. That is, the CK19 primer reagent is consumed by an amount corresponding to 8 tests.

Next, in the 3-item measurement mode, the beta actin primer reagent is aspirated from its reagent container R and discharged into four receptacles M12 different from the receptacles M12 of the reaction containers M into which the CK19 primer reagent has been dispensed. That is, the beta actin primer reagent is consumed by an amount corresponding to 4 tests.

Subsequently, four normal samples and four diluted samples are aspirated from the sample containers S. The normal samples are respectively discharged into the four receptacles M12 into which the CK19 primer reagent has been discharged, and the diluted samples are respectively discharged into the remaining four receptacles M12 into which the CK19 primer reagent has been discharged, and the normal samples are respectively discharged into the four receptacles M12 into which the beta actin primer reagent has been discharged.

Further, the enzyme reagent is aspirated from its reagent container R and discharged into the 12 receptacles M12 into which the samples have been discharged. That is, the enzyme reagent is consumed by an amount corresponding to 12 tests.

Next, each reaction container M for which the discharge has been performed is closed tight by the caps being closed by means of the cap holding member 515 of the measurement section 50. In this state, the inside of the reaction container M is heated to about 20 to 65° C. by a Peltier module (not shown) arranged below the reaction container setting part 511, and nucleic acid of the target gene (mRNA) is amplified through LAMP reaction. Then, as described above, light emitted from each light-emitter 512a transmits through a corresponding receptacle M12 of the reaction container M to be received by a corresponding light-receiver 513a. At this time, based on a detection signal from the light-receiver 513a, turbidity inside the receptacle M12 during nucleic acid amplification reaction is generated in real time. Based on the generated turbidity and the calibration curve created in advance from measurement results of the calibrators, the concentration of the target gene can be obtained from the amplification rise time. Thus, measurement of the samples ends.

Moreover, in parallel with the above measurement of the samples, measurement of the positive control and the negative control is also performed (step S315). The operation of measuring the controls in step S315 is the same as the operation of measuring the control in step S216, and thus, description thereof is omitted.

When the measurement of the samples and the measurement of the controls as described above have ended, the number of tests of the reagents used in these measurements (16 tests for the CK19 primer reagent in the 2-item measurement mode, 16 tests for the enzyme reagent in the 2-item measurement mode, 10 tests for the CK19 primer reagent in the 3-item measurement mode, 16 tests for the enzyme reagent in the 3-item measurement mode) is subtracted from the remaining number of tests in reagent information (step S316). Upon update of the remaining number of tests in the reagent information, the CPU 301 returns the processing to the main routine.

When the sample analysis process has ended, the CPU 301 causes the output section 1a to display an analysis result screen (step S109). FIG. 15 shows the analysis result screen. As shown in FIG. 15, in the analysis result screen D6, analysis results of a plurality of samples are displayed in the form of a list. The analysis result screen D6 is provided with a region A6 including a plurality of display lines. In each line of the region A6, information of measurement date, measurement time, sample ID, batch number, analysis result of CK19, and held position in the sample container setting section 10 is displayed. The analysis result of CK19 is indicated as "(Pos.)" (positive), or "(Neg.)" (negative).

Next, the CPU 301 determines whether the CPU 301 has received an instruction to shut down from the user (step S110). When having received the instruction to shut down (YES in step S110), the CPU 301 ends the processing.

On the other hand, when not having received the instruction to shut down from the user (NO in step S110), the CPU 301 returns the processing to step S106.

In step S106, when the operation mode is set to the calibration curve creation mode ("calibration curve creation mode" in step S106), the CPU 301 returns the processing to step S103 and performs the calibration curve creation order registration screen displaying process and the calibration curve creation process (step S103 and S104). In this manner, when the user selects the calibration curve creation mode, the user can perform creation of a calibration curve any time.

As described in detail above, in the sample analyzer 1 according to the present embodiment, the number of analyzable samples is calculated in consideration of measurement performed by use of calibrators and controls which are different from samples collected from subjects, and thus, an accurate number of analyzable samples can be obtained.

Other Embodiments

In the embodiment described above, description has been given of the configuration of the sample analyzer which performs measurement of calibrators and measurement of controls by using reagents, in addition to measurement of samples. However, the present invention is not limited thereto. The sample analyzer may be configured to perform measurement of controls without performing measurement of calibrators. In this case, if the sample analyzer is configured to calculate the number of analyzable samples in consideration of the amounts of reagents to be consumed in measurement of the controls, an accurate number of analyzable samples can be obtained.

Further, an apparatus configured to perform blank check in which measurement is performed by using water instead of a sample may be configured to calculate the number of analyzable samples in consideration of the amounts of reagents to be consumed in the blank check.

Further, in the embodiment described above, the gene amplification measuring apparatus has been described, but the present invention is not limited thereto. Another sample analyzer which analyzes samples using reagents, and which performs measurement of calibrators and/or controls in accordance with a predetermined rule may be configured to calculate the number of analyzable samples in consideration of the amounts of reagents to be consumed in the measurement of the calibrators and/or the controls. Examples of the predetermined rule above include a rule that calibration is performed once a week, a rule that measurement of control samples is performed per sample, and the like. Such an apparatus may be, for example, a blood cell analyzer, a blood coagulation measuring apparatus, a biochemical analyzer, a urine formed element measuring apparatus, or an immune analyzer.

Further, in the embodiment described above, when calibration curve creation is to be performed, the calibration curve creation order registration screen is displayed, and when sample analysis is to be performed, the sample analysis order registration screen is displayed. However, the present invention is not limited to the embodiment. For example, it may be configured such that the calibration curve creation order registration screen and the sample analysis order registration screen can be simultaneously displayed. Accordingly, the user can confirm at one time the number of analyzable samples when calibration curve creation is to be performed and the number of analyzable samples when sample analysis is to be performed.

Further, in the embodiment described above, a configuration in which the number of analyzable samples is calculated by use of formulae. However, the present invention is not limited thereto. For example, a look-up table showing the relationship between the remaining number of tests and the number of analyzable samples of reagents is stored in the hard disk 304 of the information processing unit 3, and by referring to this look-up table, the number of analyzable samples may be obtained.

What is claimed is:

1. A sample analyzer, comprising:
   a reagent holding section configured to hold a reagent;
   a measurement section configured to measure one or more first measurement specimens which are prepared from one or more subject samples collected from a subject and the reagent held by the reagent holding section, and to measure a second measurement specimen which is prepared from a quality control sample and the reagent held by the reagent holding section;
   an output section,
   a non-transitory memory for storing computer programs, and
   a central processing unit programmed to execute instructions from a stored program stored in the non-transitory memory, the instructions configured to cause the central processing unit to perform operations comprising:
      registering a sample analysis order for analyzing the one or more subject samples included in a batch;
      after the registration of the sample analysis order, causing the measurement section to continuously measure the one or more first measurement specimens and the second measurement specimen included in the batch; and
      causing the output section to output one or more analysis results of the subject samples included in the batch obtained by the measurement section,
   wherein when the central processing unit registers the sample analysis order, the central processing unit causes the output section to output a number of analyzable subject samples based on a remaining amount of the reagent held by the reagent holding section, an amount of the reagent required to prepare the one or more first measurement specimens and an amount of the reagent required to prepare the second measurement specimen.

2. The sample analyzer of claim 1, wherein
   the quality control sample includes a positive quality control sample and a negative quality control sample.

3. The sample analyzer of claim 1, wherein
   the instructions are configured to cause the central processing unit to perform operations further comprising:
      causing, when creating a calibration curve, the output section to output a second number of analyzable subject samples, based on: (I) a remaining amount of the reagent held by the reagent holding section, (II) the amount of the reagent required to prepare the first measurement specimen, (III) the amount of the reagent required to prepare the second measurement specimen, and (IV) an amount of the reagent required to prepare a third measurement specimen from a calibration curve creation sample and the reagent held by the reagent holding section.

4. The sample analyzer of claim 1, wherein
   the instructions are configured to cause the central processing unit to perform operations further comprising:
      controlling, when registering the sample analysis order, the output section to include the number of analyzable subject samples in a screen display for registering a sample order.

5. The sample analyzer of claim 4, wherein
   the instructions are configured to cause the central processing unit to perform operations further comprising controlling the output section to include, in the screen display, quality control sample information indicating the quality control sample.

6. The sample analyzer of claim 3, wherein
   the instructions are configured to cause central processing unit to perform operations further comprising controlling, when creating the calibration curve, the output section so as to include the second number of analyzable subject samples in a second screen for registering a creation request of a calibration curve.

7. The sample analyzer of claim 4, wherein
   when registering the sample analysis order, the instructions are configured to cause the central processing unit to perform operations further comprising causing the output section to output information indicating insufficiency of the reagent when a number of the subject samples included in the batch which have been registered on the screen display is greater than the number of analyzable subject samples.

8. The sample analyzer of claim 4, wherein
when registering the sample analysis order, the instructions are configured to cause the central processing unit to perform operations further comprising prohibiting the measurement section from measuring the first measurement specimen when a number of subject samples included in the batch which have been registered on the screen display is greater than the number of analyzable subject samples.

9. The sample analyzer of claim 6, wherein
when performing creation of the calibration curve, the instructions are configured to cause the central processing unit to perform operations further comprising causing the output section to output information indicating insufficiency of the reagent in a case where the second number of analyzable subject samples is 0.

10. The sample analyzer of claim 6, wherein
when performing creation of the calibration curve, the instructions are configured to cause the central processing unit to perform operations further comprising prohibiting the measurement section from measuring the calibration curve creation measurement specimen when the second number of analyzable subject samples is 0.

11. The sample analyzer of claim 3, wherein
the reagent holding section is configured to hold a first reagent to be used for a first analysis item, and a second reagent to be used for a second analysis item different from the first analysis item,
the measurement section is capable of measuring each of a first item measurement specimen which is prepared from a subject sample and the first reagent held by the reagent holding section, and a second item measurement specimen which is prepared from the subject sample and the second reagent held by the reagent holding section, and
the instructions are configured to cause the central processing unit to perform operations further comprising:
causing, when registering a sample analysis order for the first analysis item, the output section to output a number of analyzable subject samples based on a remaining amount of the first reagent, an amount of the first reagent required to prepare the first item measurement specimen, and an amount of the first reagent required to prepare the second item measurement specimen, and
causing, when registering a sample analysis order for the second analysis item, the output section to output a number of analyzable subject samples based on a remaining amount of the second reagent, an amount of the second reagent required to prepare the second item measurement specimen and an amount of the second reagent required to prepare the second measurement specimen.

12. The sample analyzer of claim 6, wherein
when creating the calibration curve, the instructions are configured to cause central processing unit to perform operations further comprising controlling the output section to include, in the second screen display information indicating the quality control sample to be used in the quality control.

13. The sample analyzer of claim 6, wherein
the measurement section is configured to measure a nucleic acid amplification.

14. The sample analyzer of claim 1, wherein the non-transitory memory is selected from the group consisting of read only memory and hard disc memory.

* * * * *